US007303565B2

(12) United States Patent
Buttermann et al.

(10) Patent No.: US 7,303,565 B2
(45) Date of Patent: Dec. 4, 2007

(54) APPARATUS AND METHOD FOR PERFORMING SPINAL SURGERY

(75) Inventors: Glenn Robin Buttermann, Mahtomedi, MN (US); Doug Wayne Cooper, Redwing, MN (US)

(73) Assignee: Dynamic Spine, Inc., Solana Beach, CA (US)

( * ) Notice: Subject to any disclaimer, the term of this patent is extended or adjusted under 35 U.S.C. 154(b) by 0 days.

(21) Appl. No.: 10/701,599

(22) Filed: Nov. 6, 2003

(65) Prior Publication Data

US 2004/0092943 A1 May 13, 2004

Related U.S. Application Data

(62) Division of application No. 10/043,266, filed on Jan. 14, 2002, now Pat. No. 6,761,723.

(51) Int. Cl.
*A61F 5/00* (2006.01)
*A61B 19/00* (2006.01)
(52) U.S. Cl. .......................................... 606/86; 128/898
(58) Field of Classification Search .................. 606/61, 606/79, 80, 82, 85, 176, 177, 178, 179, 180, 606/96, 86; 128/898
See application file for complete search history.

(56) References Cited

U.S. PATENT DOCUMENTS 3,426,364 A 2/1969 Lumb
4,242,758 A 1/1981 Amis et al.
4,309,777 A 1/1982 Patil
4,553,273 A 11/1985 Wu
4,586,496 A 5/1986 Keller
4,697,586 A 10/1987 Gazale
D295,317 S 4/1988 Gazale
D295,318 S 4/1988 Gazale (Continued)

FOREIGN PATENT DOCUMENTS

DE 90 00 094.3 U1 3/1991

(Continued)

OTHER PUBLICATIONS

"U.S. Markets for Adjunctive and Non-Fusion Spine Technologies", *Health Research International Division of Personal Medical Systems, Inc.*, Report #103-1-US-103, Jan. 2003, pp. 5-1 through 5-84.

(Continued)

*Primary Examiner*—Cris Rodriguez
*Assistant Examiner*—Candice C Stokes
(74) *Attorney, Agent, or Firm*—Foley & Lardner LLP

(57) ABSTRACT

A cutting guide for use in spinal surgery includes a sidewall defining an internal cavity. A chisel guide, for use with the cutting guide, includes a first block member to be inserted into the internal cavity of the cutting guide to position the first block member adjacent the vertebral body. The chisel guide also includes a second block member connected to the first block member. An apparatus for creating a cavity in a vertebral body endplate and in an intervertebral disc may be a compressor or a distractor having at least one cutting implement thereon. A tensioner determines a proper elongation distance in a prosthesis implanted in a vertebral body.

10 Claims, 22 Drawing Sheets

U.S. PATENT DOCUMENTS

| | | | |
|---|---|---|---|
| 4,759,769 | A | 7/1988 | Hedman et al. |
| 4,787,377 | A | 11/1988 | Laboureau |
| 4,911,718 | A | 3/1990 | Lee et al. |
| 4,932,975 | A | 6/1990 | Main et al. |
| 4,936,856 | A | 6/1990 | Keller |
| 5,002,576 | A | 3/1991 | Fuhrmann et al. |
| 5,015,255 | A | 5/1991 | Kuslich |
| 5,047,055 | A | 9/1991 | Bao et al. |
| 5,055,104 | A | 10/1991 | Ray |
| 5,059,193 | A | 10/1991 | Kuslich |
| 5,062,845 | A | 11/1991 | Kuslich et al. |
| 5,071,437 | A | 12/1991 | Steffee |
| 5,108,438 | A | 4/1992 | Stone |
| 5,123,926 | A | 6/1992 | Pisharodi |
| 5,141,513 | A | 8/1992 | Fortune et al. |
| 5,171,278 | A | 12/1992 | Pisharodi |
| 5,236,460 | A | 8/1993 | Barber |
| 5,246,458 | A | 9/1993 | Graham |
| 5,290,312 | A | 3/1994 | Kojimoto et al. |
| 5,306,310 | A | 4/1994 | Siebels |
| 5,314,477 | A | 5/1994 | Marnay |
| 5,336,223 | A | 8/1994 | Rogers |
| 5,360,430 | A | 11/1994 | Lin |
| 5,375,823 | A | 12/1994 | Navas |
| 5,390,683 | A | 2/1995 | Pisharodi |
| 5,397,359 | A | 3/1995 | Mittllemeier et al. |
| 5,405,391 | A | 4/1995 | Hednerson et al. |
| 5,423,816 | A | 6/1995 | Lin |
| 5,433,005 | A | 7/1995 | Cogdill et al. |
| 5,445,639 | A | 8/1995 | Kuslich et al. |
| 5,458,638 | A | 10/1995 | Kuslich et al. |
| 5,458,641 | A | 10/1995 | Ramirez Jimenez |
| 5,458,642 | A | 10/1995 | Beer et al. |
| 5,480,401 | A | 1/1996 | Navas |
| 5,480,442 | A | 1/1996 | Bertagnoli |
| 5,489,307 | A | 2/1996 | Kuslich et al. |
| 5,489,308 | A | 2/1996 | Kuslich et al. |
| 5,490,860 | A | 2/1996 | Middle et al. |
| 5,514,139 | A | 5/1996 | Goldstein et al. |
| 5,549,679 | A | 8/1996 | Kuslich |
| 5,571,189 | A | 11/1996 | Kuslich |
| 5,584,855 | A * | 12/1996 | Onik ............................ 606/207 |
| 5,591,235 | A | 1/1997 | Kuslich |
| 5,597,379 | A | 1/1997 | Haines et al. |
| 5,782,832 | A | 7/1998 | Larsen et al. |
| 5,810,827 | A | 9/1998 | Haines et al. |
| 5,827,328 | A | 10/1998 | Buttermann |
| 5,873,579 | A | 2/1999 | Prokop et al. |
| 5,893,889 | A | 4/1999 | Harrington |
| 5,897,590 | A | 4/1999 | Donovan |
| 5,928,284 | A | 7/1999 | Mehdizadeh |
| 5,951,553 | A | 9/1999 | Betz et al. |
| 5,961,522 | A | 10/1999 | Mehdizadeh |
| 5,989,256 | A | 11/1999 | Kuslich et al. |
| 6,039,763 | A | 3/2000 | Shelokov |
| 6,056,749 | A | 5/2000 | Kuslich |
| 6,056,754 | A | 5/2000 | Haines et al. |
| 6,063,121 | A | 5/2000 | Xavier et al. |
| 6,086,589 | A | 7/2000 | Kuslich et al. |
| 6,110,175 | A | 8/2000 | Scholl |
| 6,132,151 | A | 10/2000 | Courmier |
| 6,162,252 | A | 12/2000 | Kuras et al. |
| 6,174,311 | B1 | 1/2001 | Branch et al. |
| 6,209,886 | B1 | 4/2001 | Estes et al. |
| 6,231,609 | B1 | 5/2001 | Mehdizadeh |
| 6,264,695 | B1 | 7/2001 | Stoy |
| 6,287,308 | B1 | 9/2001 | Betz et al. |
| 6,383,188 | B2 | 5/2002 | Kuslich et al. |
| 6,419,704 | B1 | 7/2002 | Ferree |
| 6,454,806 | B1 | 9/2002 | Cohen et al. |
| 6,517,544 | B1 | 2/2003 | Michelson |
| 6,520,996 | B1 | 2/2003 | Manasas et al. |
| 6,527,804 | B1 | 3/2003 | Gauchet et al. |
| 6,551,320 | B2 | 4/2003 | Lieberman |
| 6,558,386 | B1 | 5/2003 | Cragg |
| 6,558,390 | B2 | 5/2003 | Cragg |
| 6,572,653 | B1 | 6/2003 | Simonson |
| 6,575,978 | B2 | 6/2003 | Peterson et al. |
| 6,582,468 | B1 | 6/2003 | Gauchet |
| 6,589,281 | B2 | 7/2003 | Hyde, Jr. |
| 6,605,648 | B1 | 8/2003 | Johnson et al. |
| 6,607,558 | B2 | 8/2003 | Kuras |
| 6,607,559 | B2 | 8/2003 | Ralph et al. |
| 6,610,093 | B1 | 8/2003 | Pisharodi |
| 6,645,249 | B2 | 11/2003 | Ralph et al. |
| 6,669,730 | B2 | 12/2003 | Ralph et al. |
| 6,673,113 | B2 | 1/2004 | Ralph et al. |
| 6,716,249 | B2 | 4/2004 | Hyde |
| 6,719,796 | B2 | 4/2004 | Cohen et al. |
| 6,733,532 | B1 | 5/2004 | Gauchet et al. |
| 6,740,117 | B2 | 5/2004 | Ralph et al. |
| 6,761,723 | B2 | 7/2004 | Buttermann et al. |
| 6,869,445 | B1 | 3/2005 | Johnson |
| 2001/0049527 | A1 | 12/2001 | Cragg |
| 2002/0016583 | A1 | 2/2002 | Cragg |
| 2002/0055740 | A1 | 5/2002 | Lieberman |
| 2002/0058944 | A1 | 5/2002 | MNichelson |
| 2003/0009224 | A1 | 1/2003 | Kuras |
| 2003/0236571 | A1 | 12/2003 | Ralph et al. |
| 2004/0002761 | A1 | 1/2004 | Rogers et al. |
| 2004/0024461 | A1 | 2/2004 | Ferree |
| 2004/0034421 | A1 | 2/2004 | Errico et al. |
| 2004/0034426 | A1 | 2/2004 | Errico et al. |
| 2004/0039448 | A1 | 2/2004 | Pisharodi |
| 2004/0044410 | A1 | 3/2004 | Ferree et al. |
| 2004/0102849 | A1 | 5/2004 | Ralph et al. |
| 2004/0111155 | A1 | 6/2004 | Ferree |
| 2004/0111156 | A1 | 6/2004 | Ralph et al. |

FOREIGN PATENT DOCUMENTS

| | | |
|---|---|---|
| DE | 94 13 778 U1 | 2/1996 |
| EP | 0 577 178 A1 | 1/1994 |
| EP | 0 948 299 B1 | 10/1999 |
| JP | 1-308557 | 12/1989 |
| JP | 5-277141 | 10/1993 |
| JP | 5-317407 | 12/1993 |
| JP | 5-508795 | 12/1993 |
| RU | 2008851 C1 | 3/1994 |
| WO | WO91/06266 | 5/1991 |
| WO | WO92/10982 | 7/1992 |
| WO | WO95/19153 | 7/1995 |
| WO | WO96/28118 | 9/1996 |
| WO | WO 03/059177 A1 | 7/2003 |

OTHER PUBLICATIONS

G. Cinotti et al., "Results of Disc Prosthesis After a Minimum Follow-Up Period of 2 Years", *Spine*, 1996, vol. 21, No. 8, pp. 995-1000, Lippincott-Raven Publishers.

M. de Kleuver et al., "Total Disc Replacement for Chronic Low Back Pain: Background and a Systematic Review of the Literature", *Eur Spin J*, 2003, vol. 12, pp. 108-116.

Von Karin Büttner-Janz et al., "Bandscheibenendoprothetik Entwicklungsweg und gegenwärtiger Stand", *Orthopädie und Traumatologie*, Mar. 1990, pp. 137-147.

Lee et al., "Development of a Prosthetic Intervertebral Disc", *Spine*, 1991, vol. 16, No. 6 supp., pp. S253-S255.

Tsuji et al., "Artificial Ceramic Intervertebral Disc Replacement in Cervical Disc Lesion", *J. West. Pac. Orthop. Assoc.*, 1990, vol. 27, No. 1, pp. 101-106.

Schmiedberg et al., "Isolation and Characterization of Metallic Wear Debris from a Dynamic Intervertebral Disc Prosthesis", *J. of Biomed. Materials Res.*, 1994, vol. 28, pp. 1277-1288.

A. D. Stefee, "The Steefee Artificial Disc", *Clinical Efficacy and Outcome in the Diagnosis and Treatment of Low Back Pain*, 1992, Chapter 24, pp. 245-257.

Langrana et al., "Finite-Element Modeling of the Synthetic Intervertebral Disc", *Spine*, vol. 16, No. 6 supp., 1991, pp. S245-252.

Büttner-Janz et al., "Biomechanics of the SB Charité Lumbar Intervertebral Disc Endoprosthesis", *International Orthopeadics (SICOT)*, 1989, vol. 13, pp. 173-176.

Enker et al., "Artificial Disc Replacement", *Spine*, 1993, vol. 18, No. 8, pp. 1061-1070.

Hedman et al., "Design of an Intervertebral Disc Prosthesis", *Spine*, 1991, vol. 16, No. 6 supp., pp. S256-S260.

Hellier et al., "Wear Studies for Development of an Intervertebral Disc Prosthesis", *Spine*, 1992, vol. 17, No. 6 supp., pp. S86-S96.

Tie-Sheng et al., "Lumbar Intervertebral Disc Prosthesis", *Chin. Med. J.*, 1991, vol. 104, No. 5, pp. 381-386.

Griffith et al., "A Multicenter Retrospective Study of the Clinical Results of the LINK® SB Charité Intervertebral Prosthesis", *Spine*, 1994, vol. 19, No. 16, pp. 1842-1849.

J. P. Kostuik, "The Kostuik Artificial Disc", *Clinical Efficacy and Outcome in the Diagnosis and Treatment of Low Back Pain*, 1992, Chapter 25, pp. 259-270.

Lee et al., Relative Efficacy of the Artificial Disc Versus Spinal Fusion, *Clinical Efficacy and Outcome in the Diagnosis and Treatment of Low Back Pain*, 1992, Chapter 23, pp. 237-243.

C. D. Ray, "The Artificial Disc", *Clinical Efficacy and Outcome in the Diagnosis and Treatment of Low Back Pain*, 1992, Chapter 21, pp. 205-225.

H. G. Edland, "Some Additional Suggestions for Intervertebral Disc Prosthesis", *J. Biomed Eng.*, 1985, vol. 7, pp. 57-62.

Urbaniak et al., "Replacement of Intervertebral Discs in Chimpanzees by Silicone-Dacron Implants: A Preliminary Report", *J. Biomed. Mater. Res. Symposium*, 1973, vol. 7, No. 4, pp. 165-186.

U. Fernström, "Arthroplasty with Intercorporal Endoprothesis in Herniated Disc and in Painful Disc", *Acta Chir Scand*, 1966, vol. 357 supp., pp. 154-159.

Fassio et al., "Prothères Discale en Silicone. Etude Expèrimentale et Premiéres Observations Cliniques", *La Nouvelle Presse Médicale*, 1978, vol. 7, No. 3, p. 207.

U. Fernström, "Intradiskal Endoprostes av Metall vid Lumbala Och Serricala Diskrupturer", *Nordisk Medicin*, 1965, vol. 73, No. 11, pp. 272-273.

H. G. Edeland, "Suggestions for a Total Elasto-Dynamic Intervertebral Disc Prosthesis", *Biomat. Med. Dev. Art. Org.*, 1981, vol. 9, No. 1, pp. 65-72.

"Compressors and Distractors", Spine Surgical Innovation, www.spinesurginnov.com, South Easton, MA.

"The Trephine System", Trephine System Technique Guide, pp. 1-11.

Mathews, et al., "Precision-Graft™ Anterior Impacted Instrumentation Set Surgical Technique", Medtronic Sofamor Danek, pp. 13, 16, 44.

Brown, et al., "Inoperative Measurement of Functional Spine Unit Stiffness", University of Miami School of Medicine, Department of Orthopaedics and Rehabilitation (R-2), http://www.mekanika.com/html/abstract/orsabstr.html, (2001).

"The first real Systems Solution to correcting spinal instability", Mekanika, www.mekanika.com.

Scott Hensley, "Artificial Spinal Disc May Open New Era in Treating Back Pain, but Worries Linger", The Wall Street Journal, Personal Journal, p. D1, Nov. 2, 2004.

M. Kanayama et al., "Intraoperative Biomechanical Assessment of Lumbar Spinal Instability: Validation of Radiographic Parameters Indicating Anterior Column Support in Lumbar Spinal Fusion", *Spine*, vol. 28, pp. 2368-2372 (2003).

"The Spinal Stabilization Company", Mekanika, 42 pp., www.mekanika.com printed from website on Aug. 9, 2005.

Mark D. Brown et al., "Measurement of Cadaver Lumbar Spine Motion Segment Stiffness", Spine, vol. 27, No. 9, pp. 918-922 (2002).

Neuro, Ortho & Spinal Surgery, SSI Ultra Instruments Catalog, pp. 1, www.specsurg.com/ultra/Neuro.cfm printed from website Aug. 10, 2005.

Noshir A. Langrana et al., "Materials and Design Concepts for an Intervertebral Disc Spacer. I. Fiber-Reinforced Composite Design", Journal of Applied Biomaterials, vol. 5, pp. 125-132, 1994.

"FDA Approves Artificial Disc; Another Alternative to Treat Low Back Pain," FDA Talk Paper, T04-45, Oct. 26, 2004.

Red Herring The Business of Technology, "Easing Back and Joint Pain", www.redherring.com, Mar. 6, 2006.

* cited by examiner

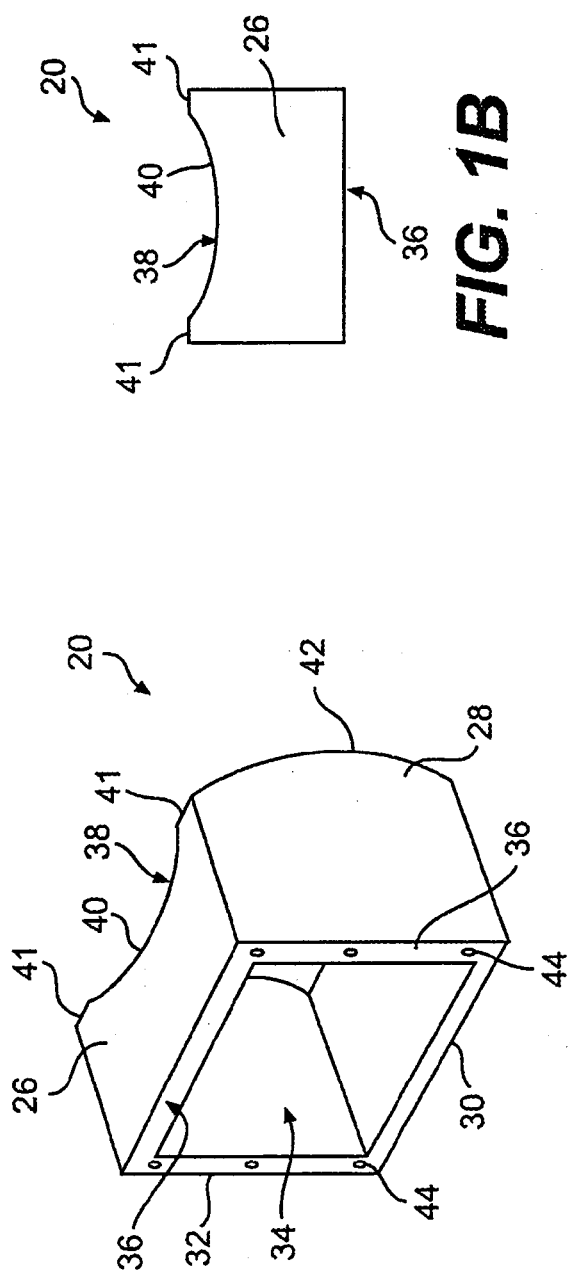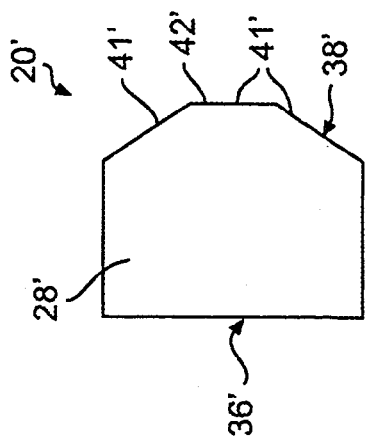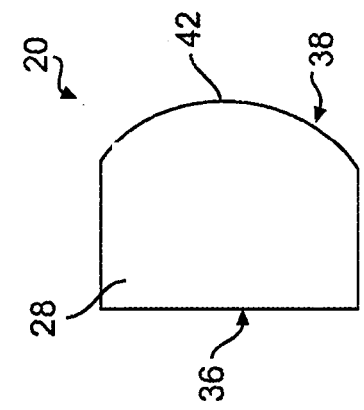

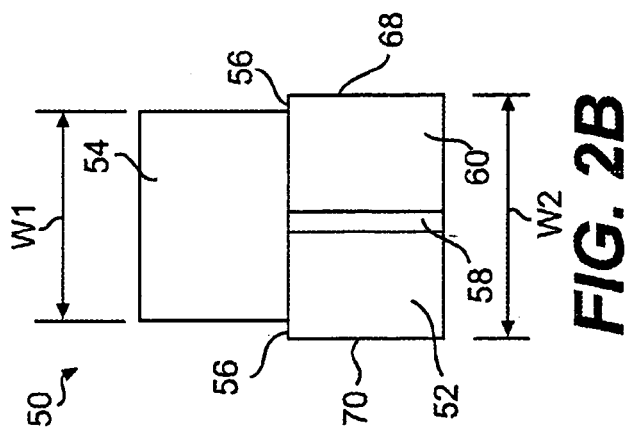
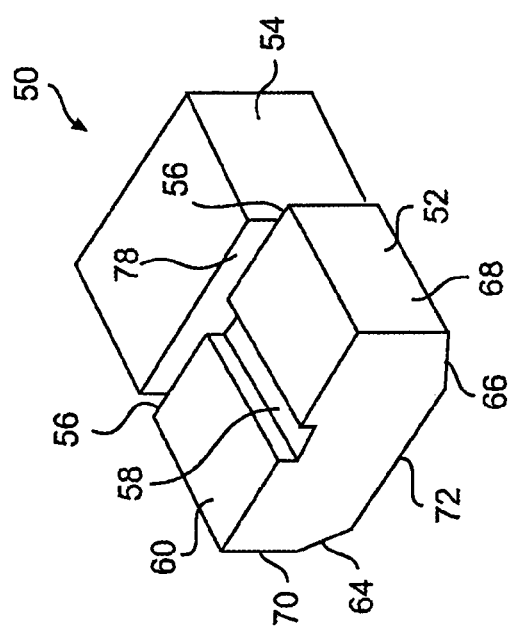
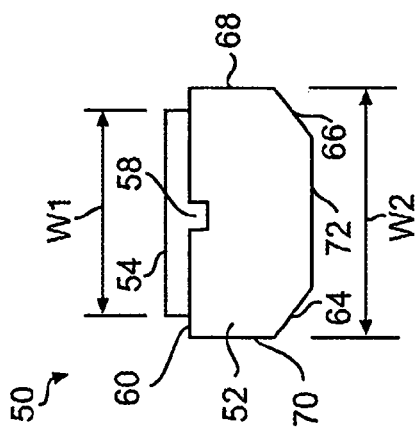
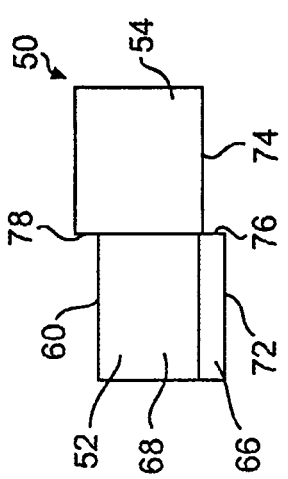
FIG. 2A
FIG. 2B
FIG. 2C
FIG. 2D

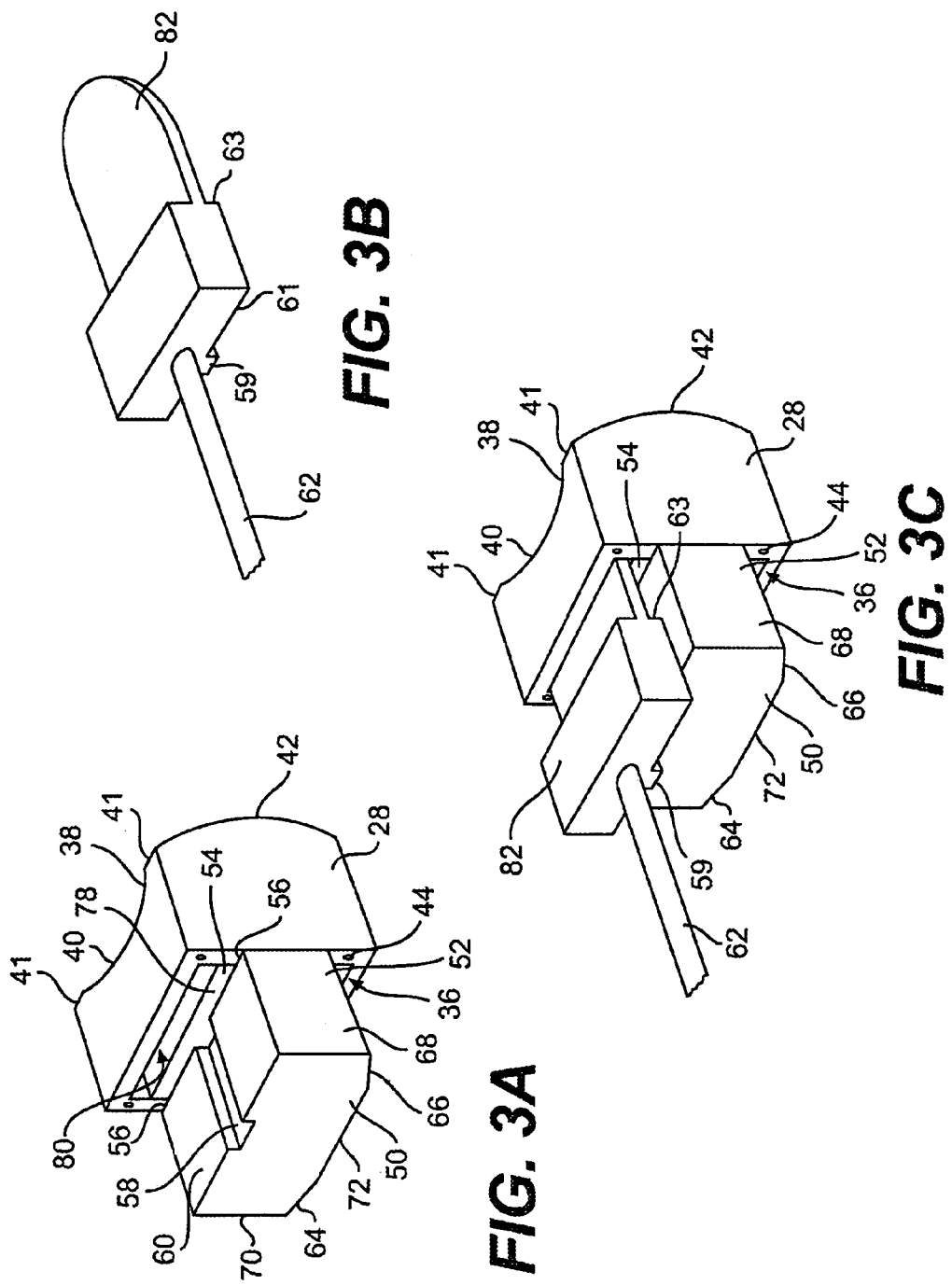

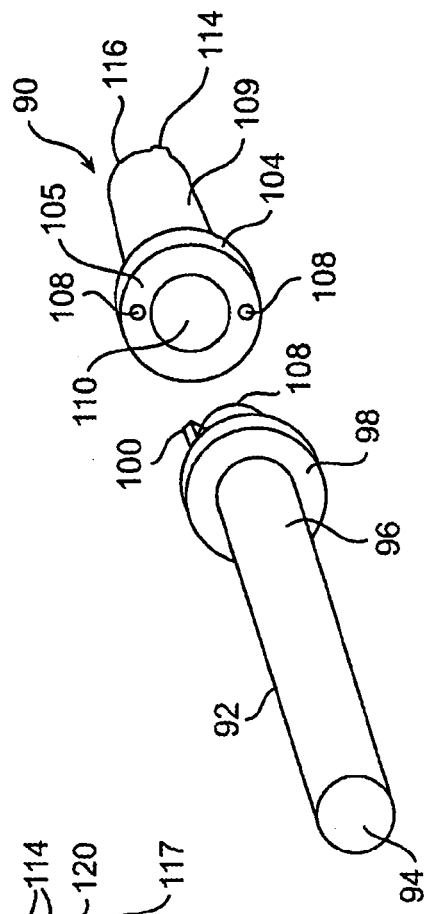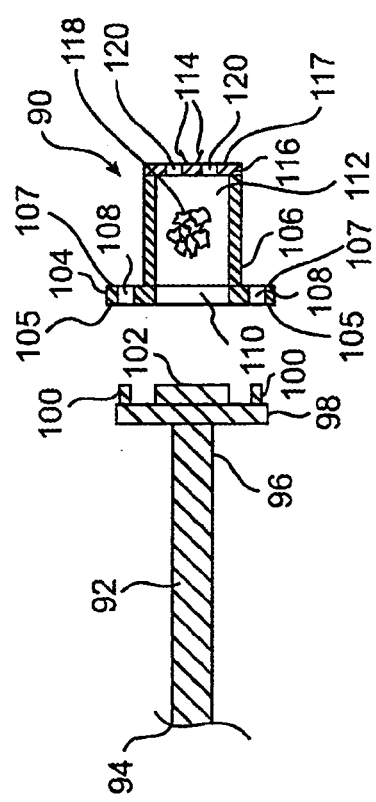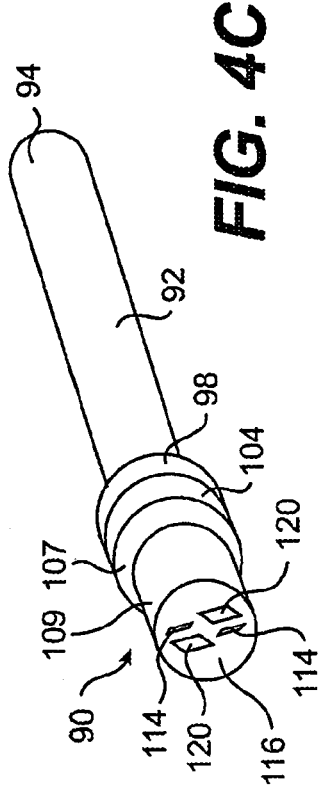

APPARATUS AND METHOD FOR PERFORMING SPINAL SURGERY

This is a divisional application of U.S. Ser. No. 10/043,266, filed Jan. 14, 2002, now U.S. Pat. No. 6,761,723 which is incorporated in its entirety by reference.

BACKGROUND OF THE INVENTION

This invention relates to the field of spinal surgery. More specifically, this invention relates to apparatuses for creating cavities in vertebral bodies and in intervertebral discs located between the vertebral bodies. This invention also relates to methods for creating such cavities. Once the cavities are created with the apparatuses and according to the methods of the present invention, an intervertebral prosthetic device, designed to replace a damaged intervertebral disc, can be implanted in the cavities. Moreover, the implanted device may be used in vertebral body fusion or in reconstruction of mobile discs through spinal arthroplasty (i.e., disc replacement).

The human spine is a flexible structure comprised of twenty-five vertebrae. Intervertebral discs separate and cushion adjacent vertebrae. The intervertebral discs act as shock absorbers and allow bending between the vertebrae.

An intervertebral disc comprises two major components: the nucleus pulposus and the annulus fibrosis. The nucleus pulposus is centrally located in the disc and occupies 25-40% of the disc's total cross-sectional area. The nucleus pulposus usually contains 70-90% water by weight and mechanically may function like an incompressible hydrostatic material. The annulus fibrosis surrounds the nucleus pulposus and resists torsional and bending forces applied to the disc. Thus, the annulus fibrosis serves as the disc's main stabilizing structure. A healthy disc relies on the unique relationship of the nucleus and annulus to one another. The top and bottom surfaces of intervertebral discs abut vertebral body endplates.

Individuals with damaged or degenerated discs often experience significant pain. The pain results, in part, from instability in the intervertebral joint due to a loss of hydrostatic pressure in the nucleus pulposus, which leads to a loss of disc height and altered-loading of the annulus fibrosis.

A conventional treatment for degenerative disc disease is spinal fusion. In one such surgical procedure, a surgeon removes the damaged natural disc and then fuses the two adjacent vertebral bodies into one piece. The surgeon fuses the vertebral bodies by grafting bone between the adjacent vertebrae and sometimes uses metal rods, cages, or screws to hold the graft in place until the graft heals. Other fusion procedures do not require surgical removal of the disc.

Although spinal fusion may alleviate pain associated with degenerative disk disease, it also results in loss of motion at the fused vertebral joint. Lack of motion at the fused site puts abnormal loads on the adjacent discs above and below the fusion. This additional pressure may cause the adjacent discs to degenerate and produce pain, thereby recreating the problem which originally existed. To remedy the problems associated with spinal fusion, various prosthetic devices were developed to replace the damaged disc with a suitable biomechanical equivalent.

Existing prosthetic devices have met with limited success in reproducing the biomechanics of a natural disc. For example, U.S. Pat. No. 4,759,769 to Hedman et al. discloses a synthetic disc having upper and lower plates hinged together. Although the hinged disc allows forward bending between adjacent vertebrae, the hinged disc does not allow axial compression or lateral flexion. Nor does it allow axial rotation of the vertebral column at the site of the implant. Therefore, the Hedman et al. device lacks many of the biomechanics of a natural disc.

Likewise, the prosthetic disc device disclosed in U.S. Pat. No. 4,309,777 to Patil does not replicate natural motion between adjacent discs. The Patil device includes two cups, one overlapping the other and spaced from the other by springs. The cups move only in a single axial dimension. Thus, the Patil device does not enable natural flexion of the spine in any direction. In addition, the highly constrained motion of the Patil device can lead to high device/tissue interface stresses and implant loosening.

Many synthetic devices connect to the vertebral bodies by conventional mechanical attachments, such as pegs or screws, which are known to loosen under cyclic loading conditions. Other synthetic devices use plastic or elastomeric components which, over a lifetime, produce debris from wear and possible unknown side effects.

In response to these and other known problems associated with synthetic prosthetic disc devices, U.S. Pat. No. 5,827,328 to Buttermann, which is incorporated herein by reference in its entirety, discloses an intervertebral synthetic prosthetic device designed to replace the biomechanical functionality of a failing intervertebral disc. One embodiment of the Buttermann device includes a first fixation member for implantation in a first vertebral body, a second fixation member for implantation in a second vertebral body adjacent the first vertebral body, and a compressible member that is positioned between the first and second fixation members. The Buttermann device overcomes the aforementioned problems with synthetic devices.

SUMMARY OF THE INVENTION

There is a need for improved apparatuses and methods by which cavities can be created in vertebral bodies and in an intervertebral disc. Once the cavities are created, an intervertebral prosthetic device designed to replace a damaged intervertebral disc, such as the one described in U.S. Pat. No. 5,827,328, can be implanted in the cavities.

In one aspect of the present invention, a cutting guide is provided for use in removing bone from a vertebral body. The cutting guide includes a sidewall that defines an internal cavity. In addition, the sidewall has (i) a first edge to face toward and to contact a vertebral body in at least three points and (ii) a second, opposite edge to face away from the vertebral body. The first edge includes at least two concave portions and at least one convex portion oriented generally perpendicular to the at least two concave portions.

The sidewall of the cutting guide may be comprised of four walls arranged to form a rectangular cross-section. At least one of the four walls may include a hole extending from the first edge to the second edge to receive a fastener therethrough. Further, the first edge of the sidewall may be concave along a first of the four walls and along an opposite second of the four walls, and it may be convex along a third of the four walls and along an opposite fourth of the four walls. The concave first edge along the first wall may be a mirror image of the concave first edge along the second wall. Similarly, the convex first edge along the third wall may be a mirror image of the convex first edge along the fourth wall. Moreover, although the concave and convex edges may each comprise one smooth surface, they also may be formed by a plurality of adjacent surfaces.

In another aspect of the invention, a chisel guide is provided for use in cutting bone of a vertebral body. The chisel guide includes a first block member to be positioned adjacent the vertebral body and a second block member connected to the first block member. The second block member has a channel, formed on one side thereof, which terminates at the first block member.

In one embodiment of the chisel guide, the first block member and the second block member may be formed as one integral piece. Further, the second block member may extend beyond the perimeter of the first block member in at least one dimension to form a shoulder with the first block member. For example, the second block member may have a width greater than the width of the first block member such that the second block member forms a pair of opposed shoulders with respect to the first member.

Another aspect of the invention relates to a cutting guide and chisel guide combination for use in removing bone from a vertebral body. The combination includes a cutting guide having a sidewall defining an internal cavity. The sidewall, in turn, has a first edge to face toward and to contact a vertebral body in at least three points and a second, opposite edge to face away from the vertebral body. The combination also includes a chisel guide. The chisel guide has a first block member and a second block member connected to the first block member. The first block member is adapted to be inserted into the internal cavity of the cutting guide to position the first block member adjacent the vertebral body such that a passage remains between a first side of the first block member and an inner surface of the sidewall of the cutting guide.

In the aforementioned cutting guide and chisel guide combination, the first and second block members may be formed as an integral piece. Moreover, the second block member may be solid. In addition, the second block member may extend beyond the perimeter of the first block member, in at least one dimension, to form a shoulder with the first block member. For example, the second block member may have a width which is greater than the width of the first block member so that the second block member forms a pair of opposed shoulders with respect to the first block member. Finally, the second block member may include a channel which is formed on one side thereof and which terminates at the first block member.

In yet another aspect of the invention, an apparatus for use in removing bone from a vertebral body is provided. This apparatus includes a shaft and a reamer. The shaft has a first end and a second end, and the second end of the shaft is connectable to a power source. The reamer is connected to the first end of the shaft. The reamer includes at least one cutting member and a collection space to collect bone fragments cut by the cutting member. A slot, through which the bone fragments pass into the collection space, is adjacent the at least one cutting member.

The reamer may be detachably connected to the first end of the shaft. In addition, the reamer may have a circular cross-section. Various power sources, such as a drill, may be used to rotate the second end of the shaft. In one embodiment, the cutting member is positioned on a bone engaging surface of the reamer. The bone-engaging surface of the reamer may be flat, except for the cutting implement and slots associated therewith.

In still a further aspect of the invention, an apparatus for creating a cavity in a vertebral body endplate and in an intervertebral disc is provided. The apparatus includes a handle, a first arm, and a second arm movable toward the first arm upon actuation of the handle. The apparatus also includes a first cutting implement that is mounted to the first arm and that has a generally circular sidewall that terminates in a first cutting edge. The first cutting edge faces away from the first arm. In one embodiment of the cavity creating apparatus, the first cutting edge also may face away from the second arm. In another embodiment, the first cutting edge may face toward the second arm.

In addition, the apparatus may also include a second cutting implement mounted to the second arm and having a generally circular sidewall that terminates in a second cutting edge, the second cutting edge facing away from the second arm and facing toward the first cutting edge so that, upon actuation of the handle, the first and second cutting edges move toward each other. The cutting edges of the cutting implements may be serrated. The cutting implements also may be rotatably mounted to their respective arms. Moreover, in an embodiment having two cutting implements, the cutting implements may be mounted to rotate about the same axis of rotation.

In yet a further aspect of the invention, a tensioner apparatus for use in determining a proper elongation distance in a prosthesis implanted in a vertebral body is provided. The tensioner apparatus includes a first arm and a second arm, each having a handle portion and a separator portion. A pivot joins the first arm to the second arm and separates the separator portions from the handle portions. In addition, at least one tension measuring element is positioned on the first arm; the tension measuring element may be a strain gage.

The tensioner apparatus also may include at least one strain gage positioned on the second arm. Moreover, the strain gages positioned on the first and second arms may be part of a Wheatstone bridge and may be positioned on the separator portions of the first and second arms, respectively.

The invention also contemplates a method of creating a cavity in a vertebral body. The cavity creating method includes removably attaching a cutting guide to an outer surface of a vertebral body. The cutting guide has a cavity therein. The method also includes puncturing through the outer surface and cortical bone of the vertebral body along a perimeter of the cavity in the cutting guide, removing the punctured cortical bone of the vertebral body to expose bone in the interior of the vertebral body, and removing the bone in the interior of the vertebral body.

The method of creating a cavity in a vertebral body may also include inserting a chisel guide in the cavity in the cutting guide. In this method, the puncturing step may include using the chisel guide to guide a chisel, having a chisel blade, along a perimeter of the cavity in the cutting guide. Alternatively, the puncturing step may be accomplished by using a motorized sagittal saw. Regardless of whether a chisel and chisel guide or a sagittal saw is used to puncture through the outer surface and cortical bone, the step of removing the bone in the interior of the vertebral body may be accomplished using a reamer.

The invention further contemplates a method of creating an intervertebral disc cavity. The method includes providing an apparatus including a first arm having a first cutting implement attached thereto, a second arm, and a handle. The method also includes positioning the first arm in a cavity in a first vertebral body, compressing the handle of compressor so that the first and second arms move in a direction towards each other, cutting through the nucleus pulposus of the intervertebral disc with the first cutting implement, and removing the nucleus pulposus of the intervertebral disc to create the intervertebral disk cavity. This method also may include positioning the second arm of the compressor in a cavity in a second vertebral body, wherein the second arm has a second cutting implement thereon; and cutting through the nucleus pulposus of the intervertebral disc with the second cutting implement.

The method for creating an intervertebral disc cavity may also include, prior to the step of positioning a first arm of a compressor in a cavity in a first vertebral body, attaching a cutting guide to a surface of the first vertebral body, the cutting guide defining a cavity; cutting through the surface and cortical bone of the first vertebral body along an inside perimeter of the cavity in the cutting guide; removing the cut cortical bone of the first vertebral body to expose bone in an interior of the first vertebral body; removing the bone in the interior of the first vertebral body to create the first vertebral body cavity; and removing the cutting guide from the first vertebral body. Further, the method also may include attaching the cutting guide to a surface of the second vertebral body; cutting through the surface and cortical bone of the second vertebral body along the inside perimeter of the cavity in the cutting guide; removing the cut cortical bone of the second vertebral body to expose the bone in the interior of the second vertebral body; and removing the bone in the interior of the second vertebral body to create the second vertebral body cavity.

In addition, the invention contemplates a method of applying a predetermined load to an implanted device. The implanted device has a fixation member implanted within a vertebral body and a compressible member implanted within an intervertebral disc. The method includes providing a tensioner including a first arm and a second arm each having a handle portion and a separator portion. A pivot pin joins the first arm to the second arm and separates the separator portions from the handle portions. At least one strain gage is positioned on the first arm. The method also includes inserting the first and the second arms into the fixation member, and moving the handle portions toward each other to thereby move the separator portions away from each other until one of the separator portions contacts an upper member of the fixation member and the other of the separator portions contacts a lower member of the fixation member. The method further includes elongating the fixation member with the tensioner, and monitoring a voltage measured by the at least one strain gage, the voltage being representative of the load applied by the tensioner and thus the reactive load experienced by the compressible member of the implanted device.

BRIEF DESCRIPTION OF THE DRAWINGS

These and other features, aspects, and advantages of the present invention will become more apparent from the following description, appended claims, and accompanying exemplary embodiments shown in the drawings, which are briefly described below.

FIG. 1A is a top perspective view of a cutting guide;
FIG. 1B is a top view of the cutting guide of FIG. 1A;
FIG. 1C is a side elevation view of the cutting guide of FIG. 1A;
FIG. 1D is a side elevation view of a cutting guide having an alternative shape;
FIG. 2A is a top perspective view of a chisel guide;
FIG. 2B is a top view of the chisel guide of FIG. 2A;
FIG. 2C is a side elevation view of the chisel guide of FIG. 2A;
FIG. 2D is a front elevation view of the chisel guide of FIG. 2A;
FIG. 3A is a top perspective view of the chisel guide inserted into the cutting guide;
FIG. 3B is a top perspective view of a chisel for use with the cutting guide and chisel guide of FIG. 3A;
FIG. 3C is a perspective view of the chisel of FIG. 3B inserted into the cutting guide and chisel guide combination of FIG. 3A;
FIG. 4A is an exploded side view, in cross section, of a rotatable shaft and reamer;
FIG. 4B is an exploded perspective view of the rotatable shaft and reamer of FIG. 4A;
FIG. 4C is a perspective view of the rotatable shaft and reamer of FIGS. 4A and 4B.

DETAILED DESCRIPTION OF THE PREFERRED EMBODIMENTS

Figure 8:
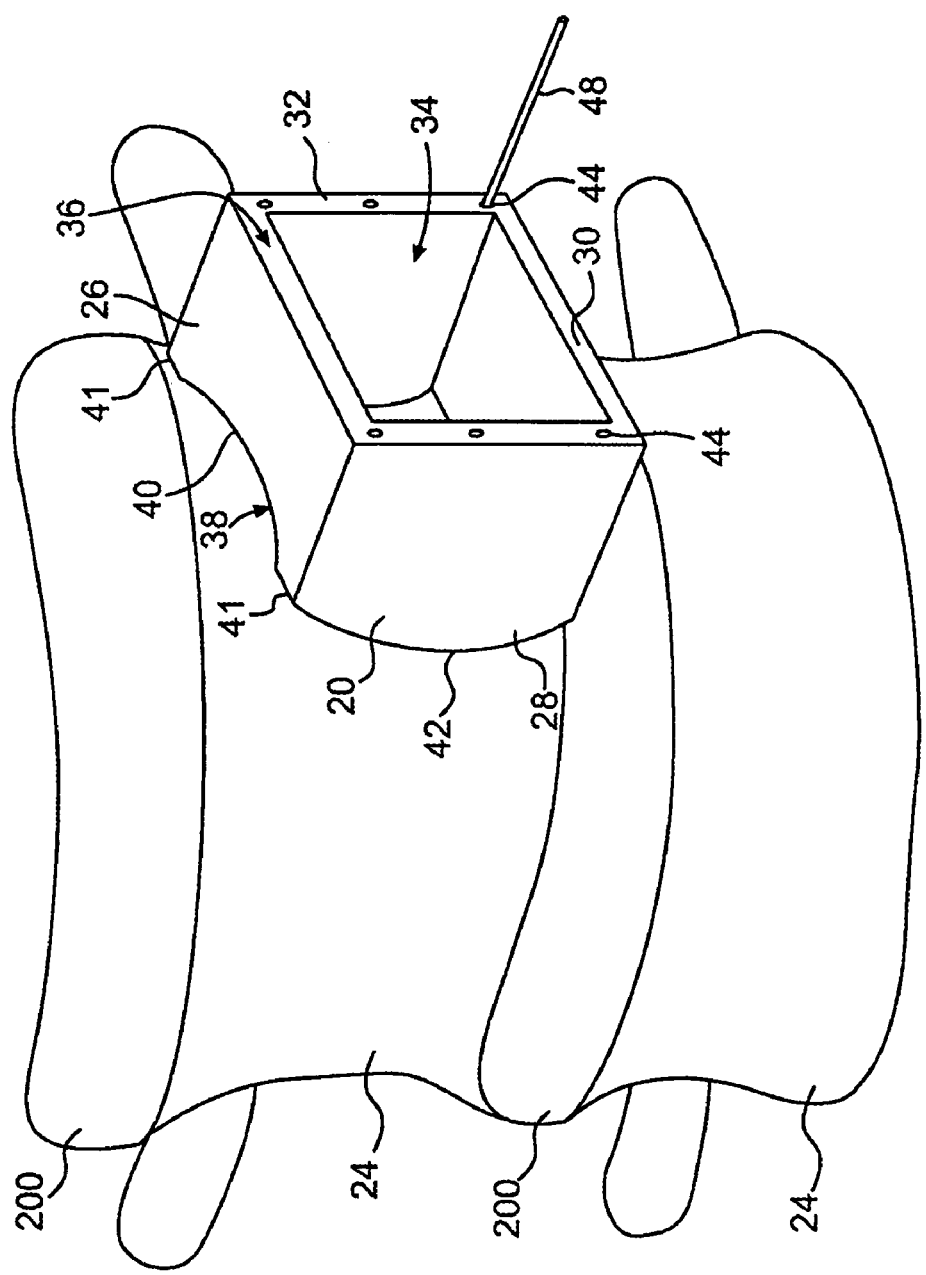
FIG. 8 is a schematic view of a cutting guide affixed to a curved surface of a vertebral body.
Figure 9A:
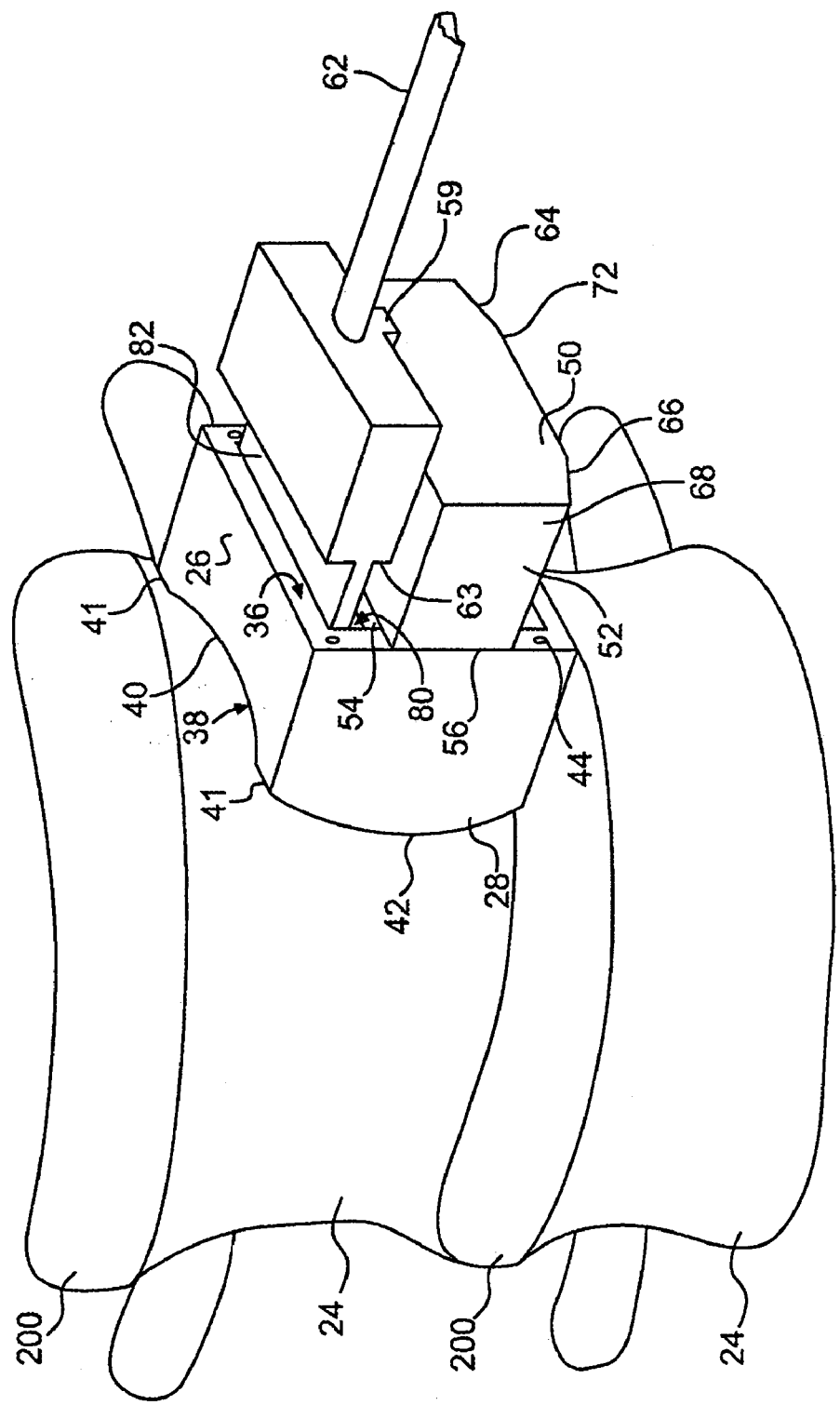
FIG. 9A is a schematic view of a cutting guide and chisel guide combination and a chisel engaged in the cutting guide and chisel combination to cut through the bone of the vertebral body.
Figure 9B:
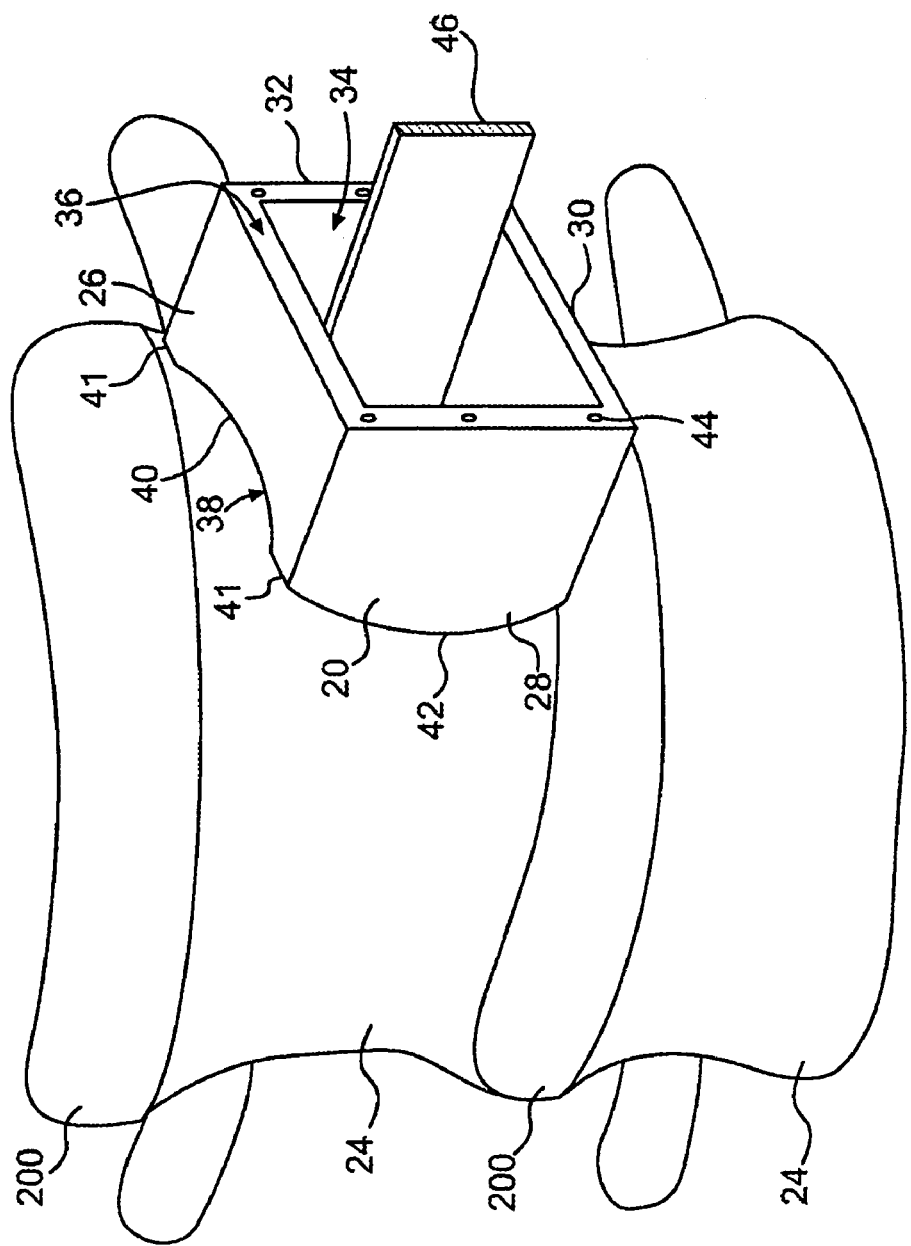
FIG. 9B is a schematic view of a cutting guide affixed to a vertebral body and a sagittal saw positioned in the cutting guide to cut through the bone of the vertebral body.

Referring now to the drawings, wherein like numerals indicate like parts, and initially to FIGS. 1A-1C and 8, there will be seen a cutting guide 20 for use in removing bone 22 from a vertebral body 24. The cutting guide is designed to be placed into contact with the outer surface of the vertebral body 24 to "guide" a surgical instrument as it cuts through the cortical bone of the vertebral body, as shown in FIGS. 8 and 9A-9B and as later described in more detail. In this regard, the cutting guide 20 has a sidewall that defines an internal cavity 34 extending through the cutting guide 20. The sidewall generally has four walls 26, 28, 30, 32 arranged to form a rectangular cross-section. Although the cavity 34 is preferably rectangular in cross-section, the walls 26, 28, 30, 32 can be configured to define a cavity that is square in cross-section or any other suitable geometric shape.

The cutting guide 20 has a first edge 38 to face toward and to contact the vertebral body 24. The cutting guide also has a second, opposite edge 36 to face away from the vertebral body 24. The first edge 38 of the cutting guide is contoured to contact the vertebral body in at least three points, although it will be understood that the first edge 38 can have four or more points of contact with a vertebral body. The first edge 38 includes both concave portions 40 and convex portions 42 configured to fit against the curved, outer surface of the vertebral body 24. The second edge 36 of the cutting guide 20 is substantially planar.

The concave portions 40 of the first edge 38 are oriented generally perpendicular to the convex portions 42. In particular, the concave portions 40 are formed along the first edge 38 of opposite walls 26, 30, and the convex portions 42 are formed along the first edge 3.8 of opposite walls 28, 32. The concave first edge along the wall 26 preferably is a mirror image of the concave first edge along the wall 30. Similarly, the convex first edge along wall 28 preferably is a mirror image of the convex first edge along wall 32. In addition, as can be seen best in FIG. 1B, the concave portion 40 of the first edge 38 of wall 26 preferably terminates before it reaches either end of the wall 26 to create flattened portions 41; the same is true of the concave portion of wall 30. These flattened portions 41 add stability to the cutting guide 20 when it is positioned against the vertebral body, as later described. Further, although the concave portions 40 and convex portions 42 may be smooth surfaces, they also may be formed by a plurality of adjacent straight surfaces. For example, as can be seen in FIG. 1C, the convex portion 42 preferably is a smooth, curved surface; however, it will be understood that the convex portion can be formed by a plurality of straight segments 41', as shown, for example, in FIG. 1D.

A plurality of holes 44 pass through the cutting guide 20 from edge 36 to edge 38. These holes 44 are adapted to receive fasteners 48, as shown in FIG. 8, to secure the cutting guide 20 to the vertebral body 24. Although the holes 44 can be positioned anywhere along edges 36, 38, it is preferable that they be positioned to extend through walls 28, 32 having convex portions 42. In addition, although FIGS. 1A-1C show six holes 44, one of ordinary skill in the art will understand that fewer or more holes can be employed in the cutting guide 20 without departing from the broadest scope of the invention. Moreover, in a cutting guide having more than four holes 44, a surgeon need not position fasteners in all holes, but, in fact, may only need fasteners in two holes 44 to secure the cutting guide 20 to the vertebral body, depending on the surface contour of the vertebral body. In one preferred embodiment, three or four holes 44 would receive a fastener 48.

Turning to FIGS. 2A-2D, there is shown a chisel guide 50 for use in cutting bone of a vertebral body 24. The chisel guide 50 can be used in combination with the cutting guide 20 to guide a chisel 62, or osteotome, as seen in FIG. 3B, toward the cortical bone 22 of the vertebral body 24. The chisel 62 then can cut through the bone 22 to expose the inside of the vertebral body 24, as will be later described in more detail. The chisel guide 50 includes a first block member 54 to be positioned towards the vertebral body 24 and a second block member 52 connected to the first block member 54. Although the blocks 52, 54 may be separate pieces joined together to form the chisel guide 50, they preferably are solid and integrally molded or machined as one piece. The second block 52 preferably extends beyond the perimeter of the first block 54 in at least one dimension to form a shoulder 56 with respect to the first block 54. For example, the first block 54 has a first width W1, and the second block 52 has a second width W2 greater than the first width W1, thereby forming opposed shoulders 56 with respect to the first block 54. In addition, the second block 52 can have a channel 58 formed in a top side 60 thereof. The channel 58 terminates at the first block 54. The channel 58 may receive a projection 59 on a chisel 62, as shown in FIG. 3B, when the chisel guide 50 is positioned in the cutting guide 20.

Although the blocks 52, 54 can have approximately the same height, they are vertically offset from each other, thereby creating two ridges 76, 78. As later described in detail, the first ridge 76, formed by part of the second block 52, is designed to engage the flat edge 36 of the cutting guide 20. Similarly, the second ridge 78, formed by part of the first block 54, serves as a chisel guiding edge by abutting a surface 63 on the chisel 62 to prevent the chisel 62 from penetrating too deep into the vertebral body 24. In this way, the surface 63 can act as a safety stop.

The second block 52 of the chisel guide 50 has two side surfaces 68, 70, a bottom surface 72, and two connecting surfaces 64, 66 extending between each side surface 68, 70 and the bottom surface 72, as shown most clearly in FIGS. 2C and 2D. The connecting surfaces 64, 66 not only make it easier to position the chisel guide 50 in the cutting guide 20, they also provide the surgeon with access to at least one hole 44 formed in edge 36 so that fasteners 48 can be driven through the holes 44 in the edge 36 while the chisel guide 50 is positioned in the cutting guide cavity 34, as shown in FIG. 3A. Accordingly, although the connecting surfaces 64, 66 are shown as being slanted, they could be any shape which provides sufficient access to holes 44 in edge 36; for example, the surfaces 64, 66 could be curved.

FIGS. 3A-3C show a combination of the cutting guide 20 and the chisel guide 50, how they engage each other, and how the chisel 62 can be inserted and guided into the cutting guide 20 by the chisel guide 50. The first block 54 of the chisel guide 50 is designed to fit in the cavity 34 of the cutting guide 20 so that the shoulders 56 and the ridge 76 of the second block 52 abut the flat edge 36 of the cutting guide 20. The shoulders 56 are designed to abut two opposite walls of the cutting guide 20 whenever the chisel guide 50 is inserted in the cutting guide 20. When so positioned, the cutting guide 20 and the chisel guide 50 create a restricted passage 80 for insertion of the chisel 62; the passage 80 is between a first side of the first block 54 and an inner surface of the sidewall of the cutting guide 20.

The passage 80 is sized so that a blade 82 of the chisel 62 can pass therethrough in a controlled direction, as shown in FIG. 3C. The chisel 62 can have a projection 59 on one side 61 thereof which slidably engages the channel 58 in the top side 60 of the second block 52. When the cutting guide 20 is affixed to a vertebral body 24, and the chisel guide 50 is positioned in the cavity 34 of the cutting guide 20 to create the, passage 80, a surgeon can insert chisel blade 82 into the passage 80 to make a straight cut into the bone 22 of the vertebral body 24. The chisel can be inserted into the restricted passage 80 until the surface 63 on the chisel 62 abuts the second ridge 78 on the first block 54. In this positions a first cut can be made into the vertebral body 24 along a first wall 26 of the cutting guide 20.

After the first cut is made, the chisel guide 50 can be rotated 180 degrees from the orientation shown in FIG. 3A to create a passage for the chisel blade 82 adjacent an opposite wall 30 of the cutting guide 20, at which a second cut can be made into the vertebral body 24. The second cut is substantially parallel to the first cut. In this regard, the first width W1 of the first block 54 preferably is less than or equal to the inner distance between the walls 28, 32.

As mentioned above, the cutting guide 20 can be rectangular or square. If the cutting guide 20 has a rectangular shape, as shown in FIG. 1A, then the surgeon can use a second chisel guide to make cuts along walls 28, 32. The first block member of this second chisel guide has a width less than or equal to the inner distance between the walls 26, 30. Using this second chisel guide, the surgeon can make third and fourth cuts substantially perpendicular to the first and second cuts along the inner edges of walls 28, 32. As a result, a substantially rectangular cut 202 can be made in a controlled manner into the vertebral body 24. This surgical technique will be described in more detail in connection with FIGS. 9A and 10.

If the cutting guide is square in shape, after the first and second cuts the surgeon can rotate a single chisel guide 90 degrees clockwise from the orientation of FIG. 3A, to make a third cut into the vertebral body along wall 28. Further, after the third cut, the surgeon can rotate the chisel guide 180 degrees, to make a fourth cut into the vertebral body along wall 32.

FIGS. 4A-4C show a reamer 90 and a rotatable shaft 92 for removing or coring bone out of the vertebral body. A first end 96 of the shaft 92 has a plate 98 affixed thereto. On the plate 98, there are a plurality of pins 100 and preferably a boss 102 that face away from a second end 94 of the shaft 92. The boss 102, which is preferably cylindrical, can matingly engage a corresponding bore 110 in the reamer 90, as later described. The second end 94 of the shaft 92 is adapted to engage a power source, such as a hand or power drill, which is adapted to rotate the shaft 92.

Referring to FIGS. 4B and 4C, the reamer 90, which is preferably circular in cross section, includes a plate 104 at a first end 106. The plate 104 is adapted to engage the plate 98 on the shaft 92. Specifically, the plate 104 has a front surface 105 with a plurality of channels 108 and a bore 110 therethrough. The bore 110 passes through a central portion of the plate 104. The channels 108 are adapted to receive the pins 100 of plate 98, and the bore 110 is adapted to fit over the boss 102, to mount the reamer 90 to the shaft 92. The pins 100 are tight-fit into the channels 108 so that when the shaft 92 is rotated, for example, by a drill, the reamer 90 is rotated in unison with the shaft 92. In addition, the reamer 90 has a collection space 112 for capturing bone shavings 118 as the reamer rotates and removes bone from the vertebral body 24.

To remove bone from the vertebral body 24, the reamer 90 includes at least one cutting member 114 positioned at a second, bone engaging end 116 of the reamer 90. The cutting member 114 preferably comprises a plurality of blades. The blades 114 extend angularly from the bone engaging end 116 of the reamer 90, as seen in FIG. 4A. A slot 120, which preferably is rectangular, is positioned adjacent each blade 114. When a surface 117 of the bone engaging end 116 of the reamer 90 is, positioned adjacent cancellous bone and rotated, the blades 114 shave through the bone and the interior of a vertebral body 24. The bone shavings 118 pass through the slots 120 and into the collection space 112. The shavings 118 can be collected and stored in the collection space 112 for later use as needed. The surface 117 of the bone engaging end 116 is flat except for blades 114 and slots 120.

Figure 11:
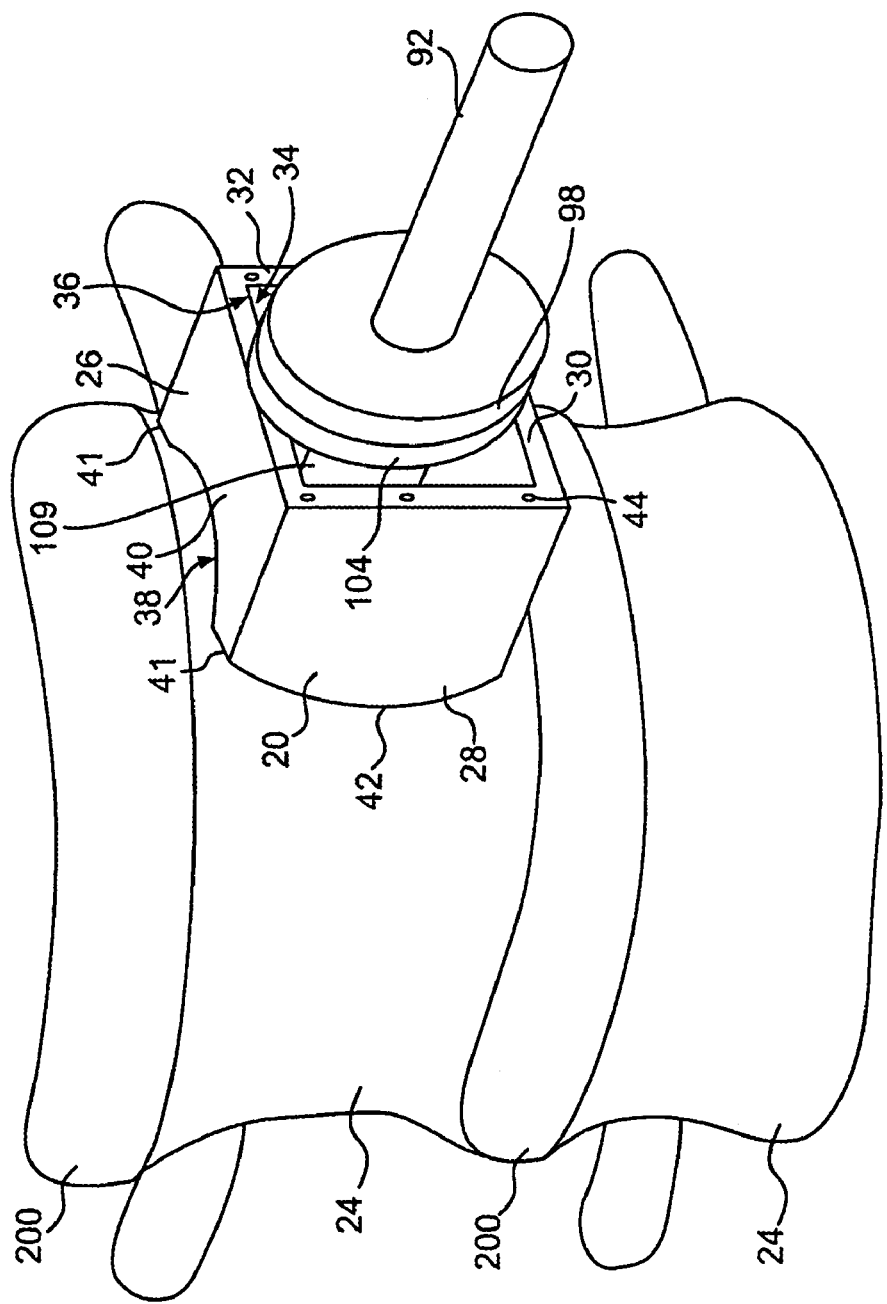
FIG. 11 is a schematic view of a reamer, positioned in the cutting guide, for drilling into the vertebral bone of the vertebral body to create a cavity.

As shown in FIGS. 4A-4C, the reamer 90 has a cylindrical portion 109 which is adapted to be journalled into the cavity 34 of the cutting guide 20, as shown in FIG. 11. The cylindrical portion 109 includes a contact surface 107 on the plate 104. The contact surface 107 is on the side opposite the surface 105 that abuts the plate 98 at the first end 96 of the shaft 92. When the cylindrical portion 109 is inserted to the maximum depth to which the surgeon should bore into a vertebral body 24, the contact surface 107 abuts the second edge 36 of the cutting guide 20. The contact between the plate 104 and the second edge 36 of the cutting guide 20 prevents the surgeon from inadvertently reaming too far into the vertebral body 24.

Figure 5C:
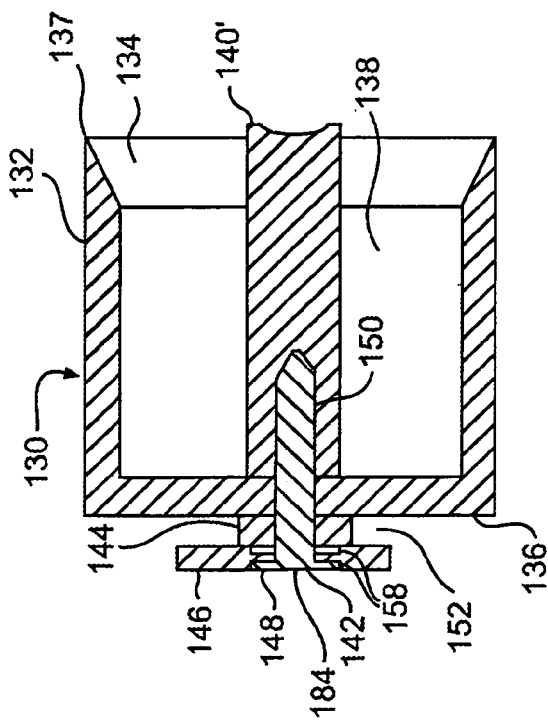
FIG. 5C is a side elevation section view, in cross section, of an alternative embodiment of the endplate and nucleus cutter.
Figure 5B:
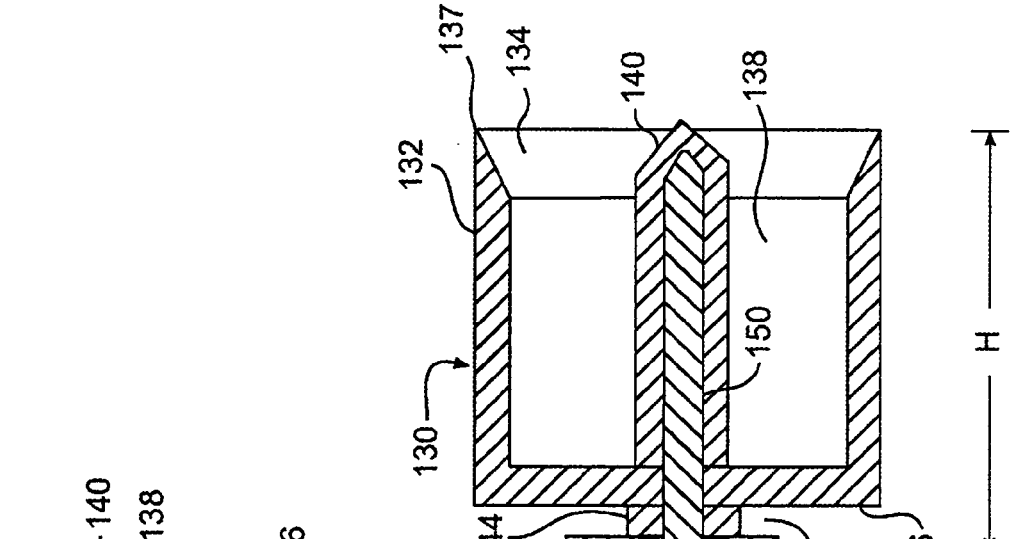
FIG. 5B is a side elevation sectional view, in cross section, of the endplate and nucleus cutter of FIG. 5A.
Figure 5A:
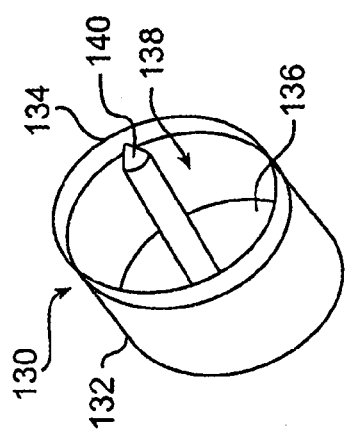
FIG. 5A is a perspective view of an endplate and nucleus cutter.

Referring now to FIGS. 5A-5C and 6A-6C, a cutting implement that can be mounted to a compressor 160 or a distractor 500 in accordance with the invention will now be described. The cutting implement can be made to cut through an endplate (208 in FIG. 13) of a vertebral body 24 and the nucleus pulposus of the intervertebral disc 200 adjacent the vertebral body 24. Turning first to FIGS. 5A-5B, there is shown an example of a cutting implement which may be used in conjunction with the compressor 160 or distractor 500. Specifically, the exemplary cutting implement is in the form of an endplate and nucleus cutter 130 having a substantially circular sidewall 132 that terminates in a cutting edge 134. The diameter of the substantially circular sidewall will depend on the size of the nucleus pulposus to be removed. The maximum diameter of the sidewall should be greater than the minimum diameter of the nucleus pulposus and/or the diameter of the prosthesis 220, 230 to be implanted. In addition, the cutting edge 134 can be smooth or, alternatively, serrated. The cutting edge 134 may be thinner than the sidewall 132 and may be tapered to a sharp end 137. In addition, the endplate and nucleus cutter 130 has a base 136 to which the sidewall 132 is attached. The base 136 and the sidewall 132 define an essentially hollow cylindrical cavity 138. Extending from the base 136 in the cavity 138 is a projection 140 that contains a screw hole 188 adapted to receive a screw 142. Although the projection 140 may extend only part way into the cavity 138, it can extend beyond the sharp edge 137, as shown in FIG. 5B. In the embodiment of FIG. 5B, the tip of projection 140 can be used to create a notch in an endplate, thereby bracing the endplate and nucleus cutter 130 relative to the endplate.

The projection 140 then can serve as an axis of rotation. This bracing effect enables a surgeon to cut through the endplate with the sharp end 137 of the endplate and nucleus cutter 130 without risk that the endplate and nucleus cutter 130 will inadvertently slide from its proper position relative to the endplate surface.

An alternative embodiment of the endplate and nucleus cutter 130 is shown in FIG. 5C. The only difference between this embodiment and the one shown in FIG. 5B is that the projection 140' is cylindrical in shape and has a concave end. An advantage of employing the embodiment of FIG. 5C with the embodiment of FIG. 5B on a single compressor 160 is that when the sharp edges 137 of the two endplate and nucleus cutters 130 approach each other, the tip of the projection 140 will be partially journalled into the concave end portion of the projection 140'.

Figure 6A:
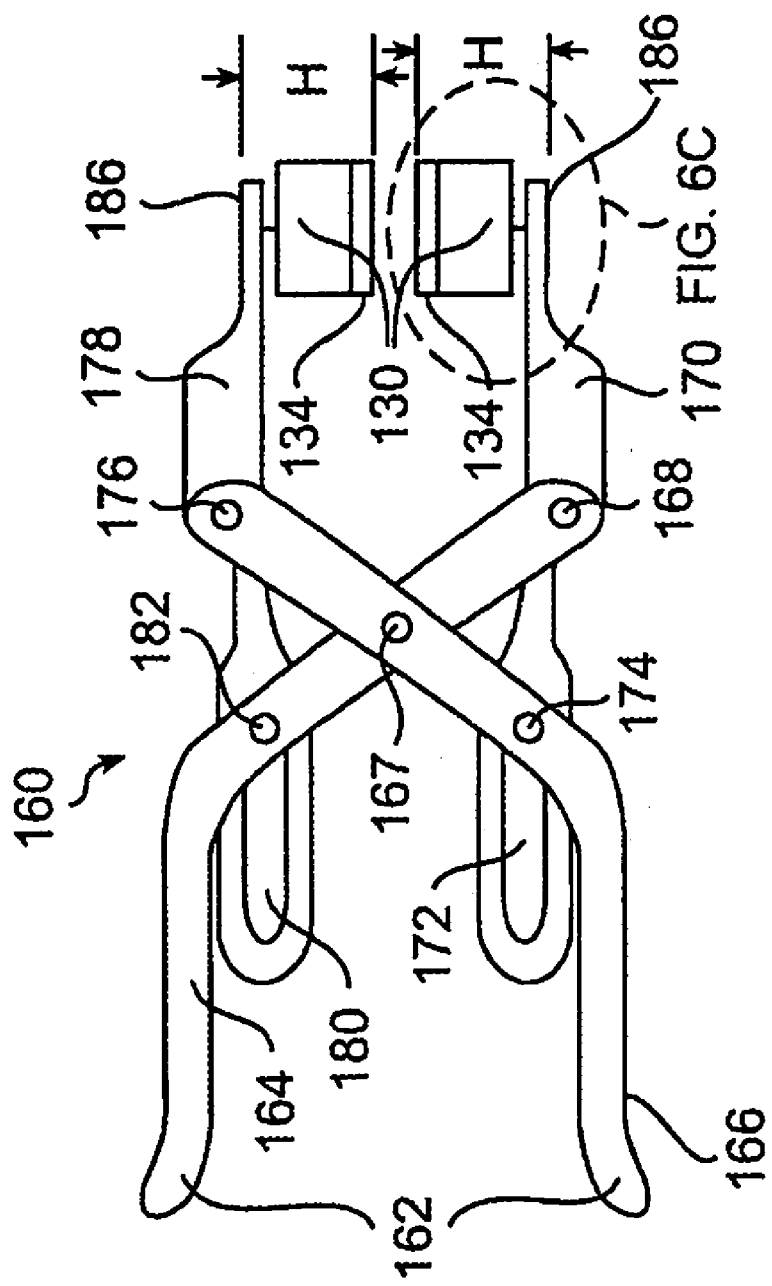
FIG. 6A is a side elevation view of a compressor having a pair of endplate and nucleus cutters mounted thereto.

With respect to FIG. 6A, the compressor 160 includes a handle 162, which has two scissor-like members 164, 166 pivotally joined at a pivot 167, such as a pin. The first member 164 is joined at a pin 168 to a first arm 170. A channel 172 is located in the first arm 170, and a projection pin 174 extending from the second member 166 can slide in the channel 172. Similarly, the second member 166 is joined at a pin 176 to a second arm 178. The second arm 178 is substantially parallel to the first arm 170. In addition, like the first arm 170, the second arm 178 has a channel 180 in which a projection pin 182 extending from the first member 164 can slide.

In the preferred embodiment shown in FIG. 6A, an endplate and nucleus cutter 130 is attached to an end portion 186 of the first arm 170 and faces toward the second arm 178. Similarly, an endplate and nucleus cutter 130 is attached to an end portion 186 of the second arm 178 and faces toward the first arm 170 (i.e., toward the other endplate and nucleus cutter 130).

When the handle 162 is compressed by pressing members 164, 166 toward each other, the projection pins 174, 182 slide in their respective channels 172, 180, and the first and second arms 170, 178 move toward each other in parallel. In addition, as the first and second arms 170, 178 move toward each other, the arms 170, 178 maintain their approximately parallel orientation. Moreover, as the first and second arms 170, 178 approach each other in parallel, the endplate and nucleus cutters 130 also approach each other. Preferably, the endplate and nucleus cutters 130 on the first and second arms 170, 178 share a common central-axis so that, when the handle 162 is fully compressed, the cutting edges 134 of the endplate and nucleus cutters 130 on the first and second arms 170, 178 contact each other.

The endplate and nucleus cutters 130 can be either fixedly mounted or rotatably mounted to the arms 170, 178 of the compressor 150. When the endplate and nucleus cutters 130 are fixedly mounted, the surgeon can manually rotate the cutters 130 by swinging the handle 162 of the compressor 150 side-to-side. This side-to-side motion, combined with compression of the handle 162, enables the cutting edges 134 to cut through the endplate and nucleus pulposus of the damaged disc. Alternatively, the endplate and nucleus cutters 130, may be rotatably mounted to the compressor. A motor or other drive source can be connected to the cutters 130 to rotate them relative to the arms 170, 178 of the compressor 150.

The compressor 160 is shown having two endplate and nucleus cutters 130 thereon which face inward and toward each other. The compressor 160 is used, as later explained in detail, when a surgeon wants to implant a prosthetic device 220 having two fixation members 222, one of which is to go into a vertebral body 24 above a problematic disc 200 and the other of which is to go into the vertebral body 24 below the problematic disc.

Figure 6B:
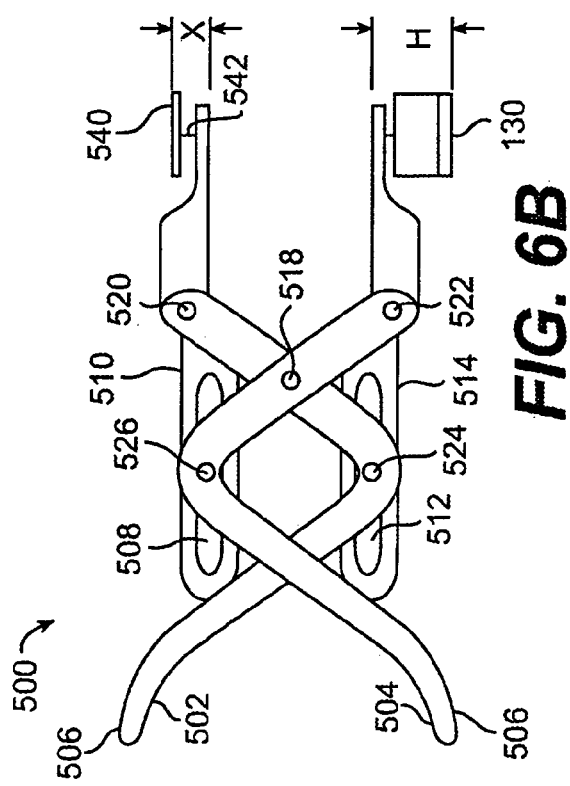
FIG. 6B is a side elevation view of a distractor having one endplate and nucleus cutter mounted thereto.
Figure 19A:
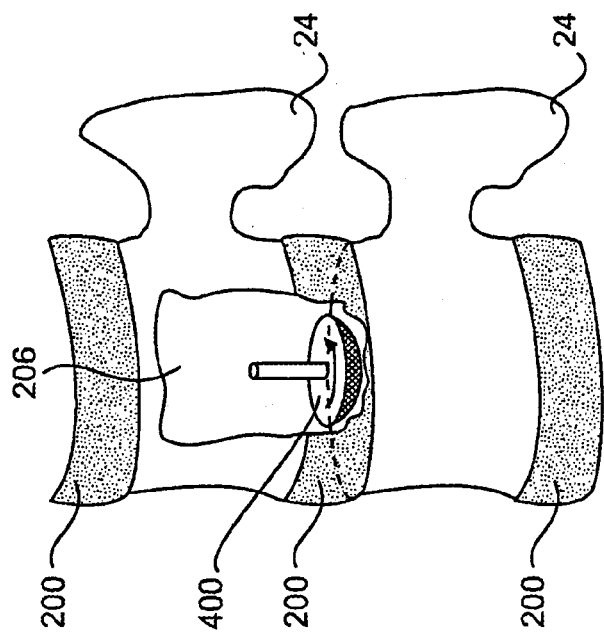
FIG. 19A is a schematic view of a rotatable dome-shaped cutter.
Figure 19B:
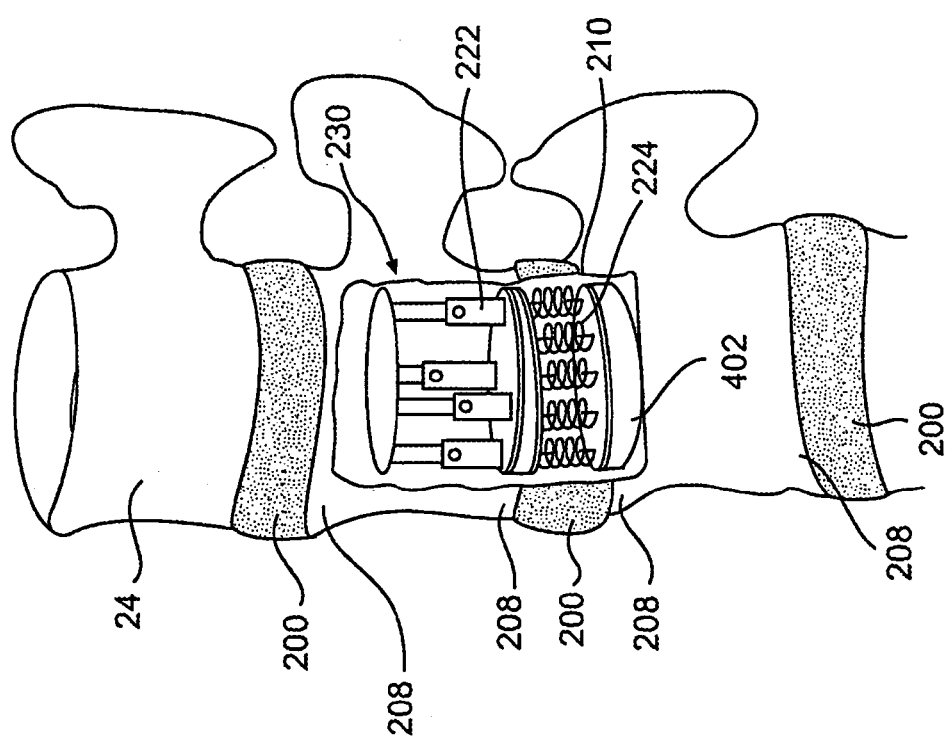
FIG. 19B is a schematic, cut-away left side view of a vertebral body having a cavity formed therein by the rotatable dome-shaped cutter of FIG. 19A.

In some situations, however, the surgeon needs to implant only one fixation member 222, for example, as shown in FIG. 19B, and as will be described below. In such situations, a distractor 500, which has one outwardly facing endplate and nucleus cutter 130 is preferred. FIG. 6B shows a distractor 500 having one endplate and nucleus cutter 130 on a first arm 514 which faces outward and away from a second arm 510. Similarly, an outwardly facing plate 540 is rotatably attached to the second arm 510 by means of an axle 542. The plate 540 is designed to be placed against an endplate in a vertebral body and to remain immobile relative thereto. As the endplate and nucleus cutter 130 of the distractor 500 is either manually rotated by the surgeon (in an embodiment where the endplate and nucleus cutter 130 is fixedly mounted to the distractor 500) or rotates as a result of a motor applied thereto (in an embodiment where the endplate and nucleus cutter 130 is rotatably mounted to the distractor 500), the endplate and nucleus cutter 130 will cut through one endplate in a vertebral body 24, while the plate 540 remains pressed against the other endplate in the vertebral body 24. The plate 540 does not abrade the vertebral body against which it is placed because it does not rotate with respect to that endplate.

The distractor 500 has two scissor-like members 502, 504 which together form a handle 506. The scissor-like members 502, 504 are rotatably attached to one another by a pin 518. In addition, the first scissor-like member 504 is rotatably connected to the first arm 514 by means of a pin 522. A projection pin 526 extending from the first scissor-like member 504 is adapted to slide in a slot 508 in the second arm 510. Similarly, the second scissor-like member 502 is rotatably connected to the second arm 510 by means of a pin 520. Further, a projection pin 524 extending from the second scissor-like member 502 is adapted to slide in a slot 512 in the first arm 514.

When the handle 506 of the distractor 500 is compressed, the handle members 502, 504 pivot with respect to each other at pin 518, thereby correspondingly increasing the distance between the projection pins 524, 526. As the distance between the projection pins 524, 526 increases, the pins slide forward in their respective slots 512, 508. Simultaneously, the distance between the rotating pins 522, 520 and hence the distance between the first and second arms 514, 510 increases. In this manner, by compressing the handle 506, a surgeon can produce parallel distraction of the arms 510, 514 to increase the distance between the endplate and nucleus cutter 130 and the plate 540.

When the arms 514, 510 of the distractor 500 are inserted into a cavity 206 in a vertebral body 24 and the handle is subsequently compressed, the plate 540 will move in one direction to contact the endplate 208 of the vertebral body 24, whereas the endplate and nucleus cutter 130 will move in an opposite direction to contact the other endplate 208 of the vertebral body 24. Continued compression of the distractor 500 and rotation of the endplate and nucleus cutter 130 will force the cutter 130 through the endplate 208 and nucleus pulposus of the intervertebral disc 200 adjacent thereto.

Figure 6C:
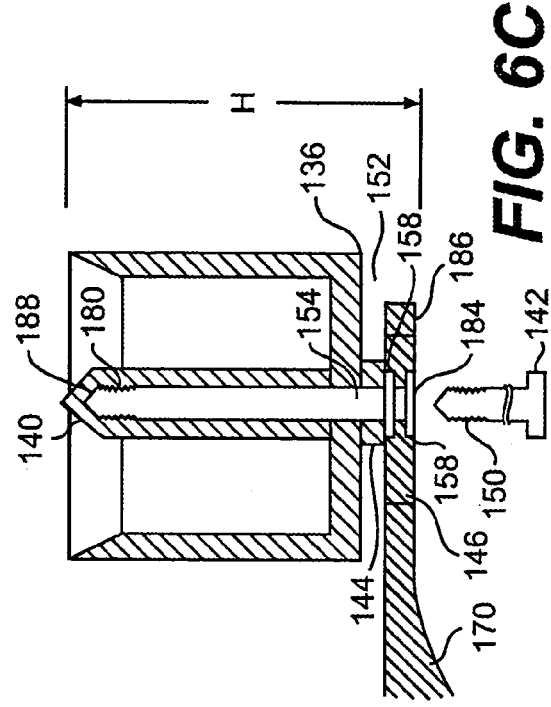
FIG. 6C is an enlarged side elevation view, in cross section, of encircled area 6C-6C in FIG. 6A with the screw removed.

Various methods exist by which an endplate and nucleus-cutter can be connected to an arm 170, 510 of a compressor 160 or distractor 500, respectively. For example, as shown in FIGS. 5B and 6C, the head 148 of the screw 142 is contained within a connective plate 146, which forms part of an arm 170, 178 of the compressor 160 or an arm 510, 514 of the distractor 500. The threaded portion 150 of the screw 142 passes through a spacer 144 and the base 136 and terminates in the projection 140. The connective plate 146 has a hole 184 through which the threaded portion 150 of the screw 142 passes; the diameter of the hole 184 in the connective plate 146 is smaller than the diameter of the head portion 148 of the screw. The height of the head portion 148 is approximately the same as that of a recess 158 in plate 146, thereby allowing the head portion 148 to sink into the connective plate 146, as shown in FIG. 5B.

The preceding discussion provides one way in which the endplate and nucleus cutter 130 can be fixedly mounted to the end portion 186 of the arm of a compressor 160 or a distractor 500. However, those of ordinary skill in the art will understand that the endplate and nucleus cutter 130 can be mounted to the end portion 186 in other ways. For example, in one preferred method, which is more permanent and integral in nature, the endplate and nucleus cutter is attached to the end portion 186 by riveting or otherwise suitably fastening the base 136 directly to the end portion 186, without use of a connective plate 146 or a spacer 144.

Moreover, the screw 142 could be adapted to be connected to (or be part of) a rotatable shaft which, in turn, is connected to a motor, such as a drill, to provide automatic rotation of the endplate and nucleus cutter 130. In this manner, the endplate and nucleus cutter 130 can be mounted so that the connective plate 146 can rotate independently of the compressor 160 or distractor 500 (if driven, for example, by a motor, not shown). Rotation of the connective plate 146 will cause a corresponding rotation of the endplate and nucleus cutter 130 attached thereto. Rotational friction can be avoided due to a gap 152 between the plate 146 and the base 136 generated by the spacer 144. Moreover, if the two endplate and nucleus cutters 130 of FIG. 6A are mounted to rotate, they can share generally the same axis of rotation.

Finally, it should also be readily apparent to one of ordinary skill in the art that the endplate and nucleus cutter 130 could have a cutting surface similar to the surface 117 of the bone engaging end 116 of the reamer 90 shown in FIGS. 4A-4C.

The preceding discussion, provided a general description of how the endplate and nucleus cutter 130 can be attached to the compressor 160 and distractor 500. A detailed description follows. To attach the endplate and nucleus cutter 130 to the compressor 160, the spacer 144 is positioned on the side of the arm 170, 178 from which the endplate and nucleus cutter 130 is to project. The spacer hole 154 is aligned with the hole 184 through the connective plate 146. The endplate and nucleus cutter 130 is then centrally positioned on top of the spacer 144 so that hole 188 in the projection 140 is aligned with both the hole 154 in the spacer 144 and the hole 184 in the connective plate 146. The threaded portion 150 of screw 142 is then inserted through the hole 184 in the connective plate 146 and the hole 154 in the spacer 144 until the threaded portion 150 engages a mutually engaging threaded portion 156 of the hole 188. By turning the screw 142, the threaded portion 150 of the screw 142 engages the threaded portion 156 of the hole 188, thereby holding the endplate and nucleus cutter 130 onto the arm 170. In addition, the head portion 148 of the screw 142 is received by the recess 158 in the connective plate 146, thereby minimizing height H. Various alternative methods may be used to attach the endplate and nucleus cutter 130 to the arms 170, 178 of a compressor 160; however, the height H (as shown in FIG. 6C) should be less than the height of the cavity 206 formed in vertebral body 24, as later described.

Connecting the endplate and nucleus cutter 130 to the distractor 500, as shown in FIG. 6B, is readily achieved by inverting the orientation of the endplate and nucleus cutter of FIG. 6A. If this orientation is chosen, a recess, similar to the recess 158 formed on the side of the arm 170 shown in FIG. 6C (i.e., adapted to receive the head portion 148 of the screw 142) should be formed on the other side of the arm 170. However, as both the first and second arms 514, 510 of the distractor will be inserted into the same cavity 206, the height (H) of the first arm 514 (with the endplate and nucleus cutter 130 attached thereto) plus the height (X) of the second arm 510 (with the plate 540 attached thereto) must be less than the height of the cavity 206 in the vertebral body 24.

In mounting the endplate and nucleus cutter 130 to create the embodiment shown in FIG. 6B, the surgeon must place the spacer 144 on the opposite side of the arm 170 as that shown in FIG. 6C. When this is completed, the screw 142 can be journalled through a hole 184 in the arm 514 and through the hole 154 in the spacer 144, in a manner similar to that of the embodiment shown in FIG. 6C. The threaded portion 150 of the screw 142 may then engage the correspondingly threaded portion 156 in the projection 140, thereby holding the endplate and nucleus cutter 130 against the arm 514.

It will be understood that an endplate and nucleus cutter 130 can be mounted to devices having a configuration different than the compressor 160 and distractor 500. For example, an endplate and nucleus cutter 130 can be attached to an end of a single arm, and a surgeon can grip the opposite end of the single arm to position the endplate and nucleus cutter 130 appropriately to cut through the endplate and the nucleus pulposus of a damaged disc. The single arm can be bent to provide additional leverage.

Figure 7:
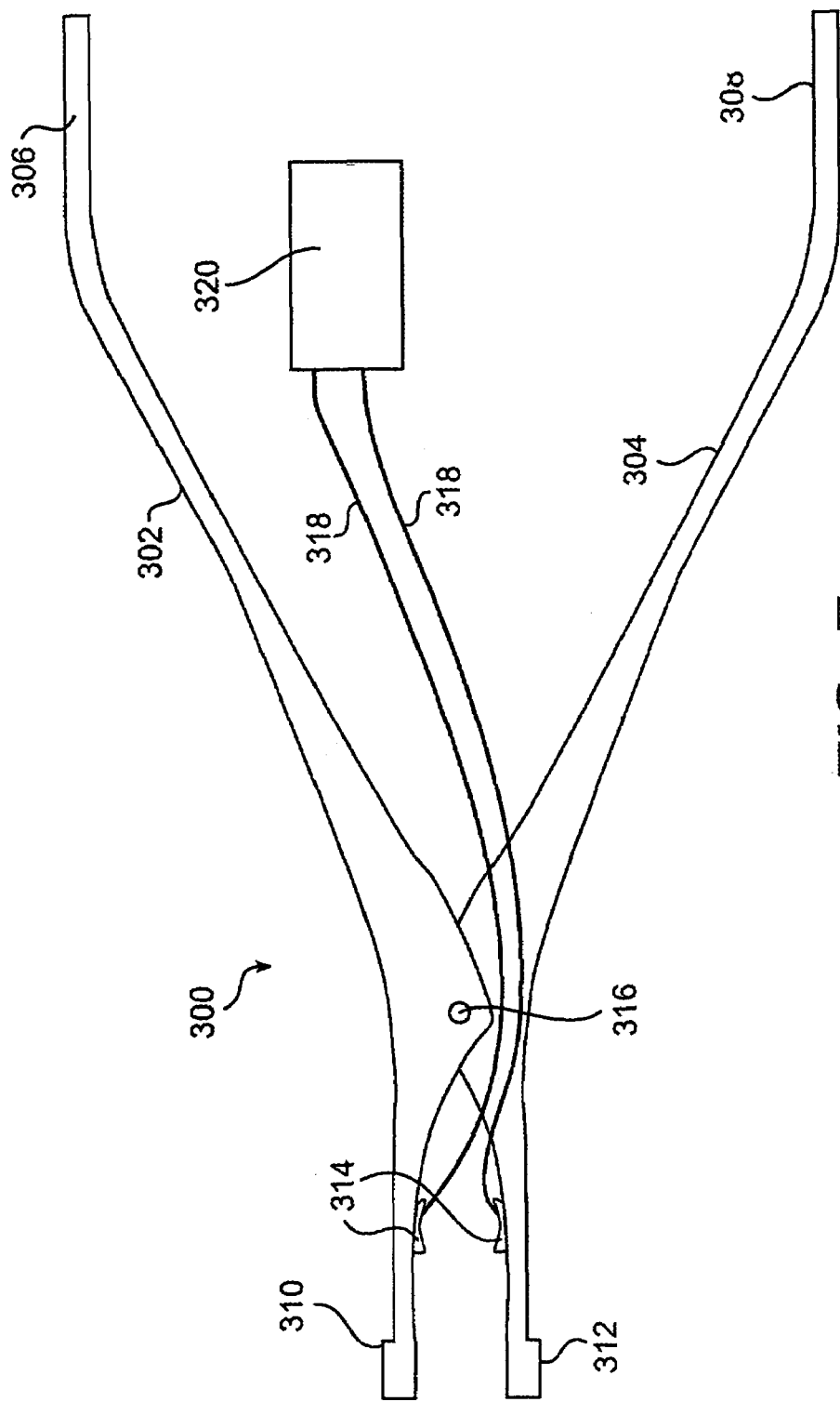
FIG. 7 is a side elevation view of a tensioner apparatus.
Figure 13:
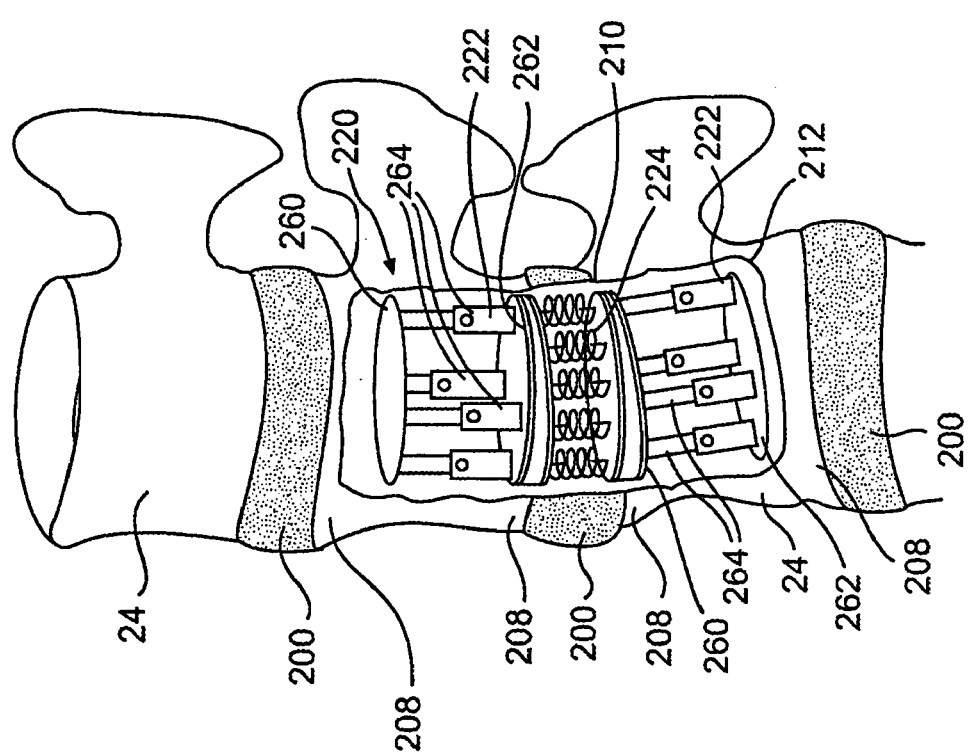
FIG. 13 is a schematic, cut-away left side view of an intervertebral prosthetic device implanted in adjacent vertebral bodies and in an intervertebral disc.
Figure 14:
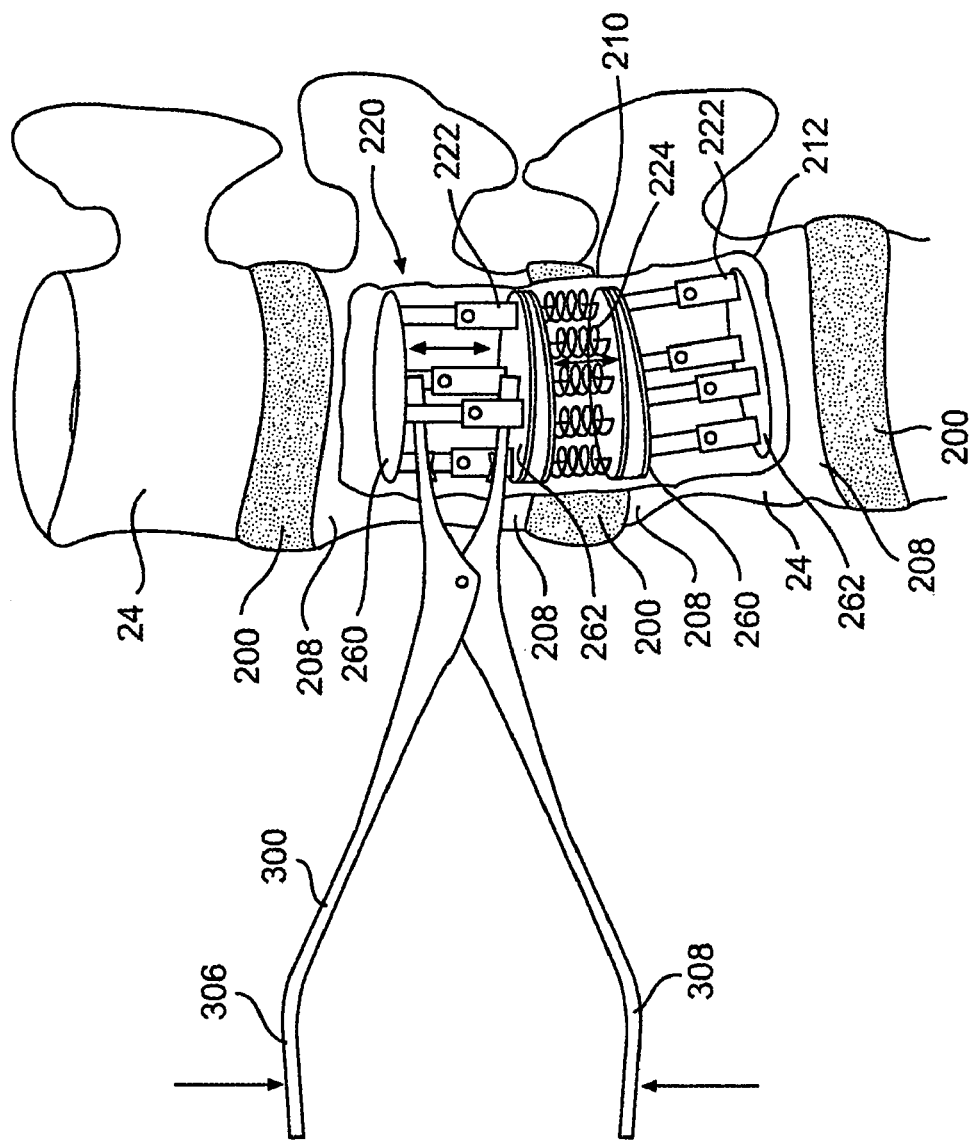
FIG. 14 is a schematic, cut-away left side view of a cavity in a vertebral body, showing the tensioner positioned therein.
Figure 18:
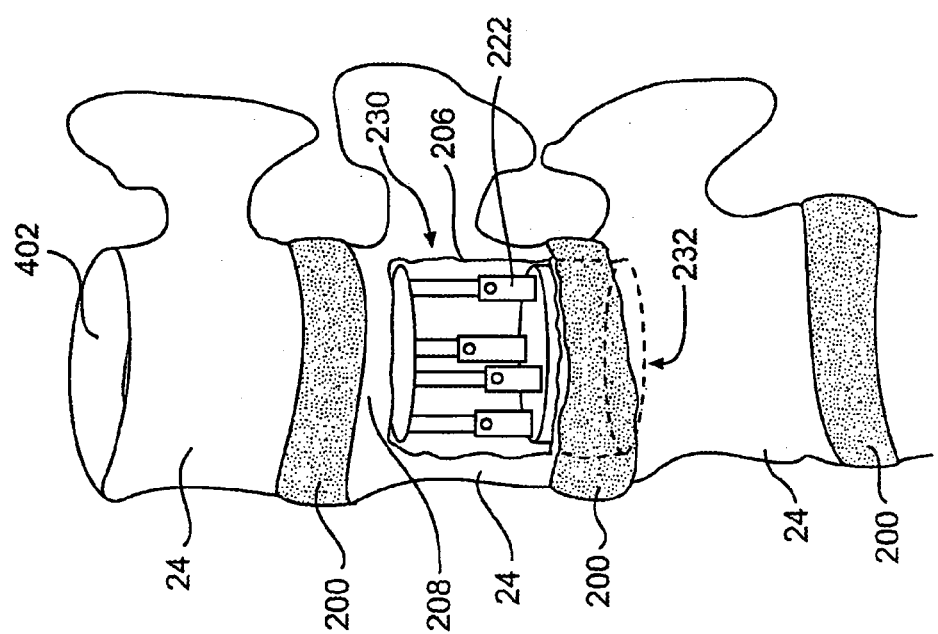
FIG. 18 is a schematic, cut-away left side view of the vertebral body and intervertebral disc of FIG. 17B having a prosthetic device positioned therein.

After a cavity is formed in the intervertebral disc 200 by either the compressor 160 or the distractor 500, an appropriate prosthetic device is implanted in the cavity. The implanted device can include two fixation members 222 and a compressible member 224, as shown in FIG. 13, or, in an alternative embodiment, the implanted device 230 can include a single fixation member 222 and a compressible member, as shown in FIG. 18. Once the implanted device is in place, the surgeon must restore the intervertebral distance, i.e., the distance between two adjacent vertebrae; this is achieved by tensioning the implanted device. That is, the load applied by the implanted device between the vertebrae on opposite sides of the excised, damaged intervertebral disc should be sufficient to recreate the approximate disc height of a healthy intervertebral disc. To do so, the surgeon can use a tensioner 300, as shown in FIG. 7. The tensioner 300 can be used to measure the tension or load applied to the compressible member 224 by the fixation member(s) 222. That is, the tensioner 300 can be used to determine when the fixation member 222 has been elongated sufficiently to apply the proper force (or load) on the compressible member 224, as will be more fully described in connection with FIG. 14.

The tensioner 300 shown in FIG. 7 includes first and second arms 302, 304, each of which has a handle portion 306, 308 and a separator portion 310, 312. The arms 302, 304 are connected by a pivot pin 316, which separates the separator portions 310, 312 from the handle portions 306, 308. Positioned on at least one (and preferably both) of the separator portions 310, 312 is at least one tension measuring element. The tension measuring element preferably, is a strain gage 314 comprised of resistors or other suitable load cell devices. It should be understood, however, that the tension measuring element may be a torque needle, a spring, a transducer other than a strain gage, or other suitable device for measuring tension. The strain gages 314 can be cemented, glued, or otherwise fastened on the separator portions 310, 312. In a preferred embodiment, the strain gages 314 are part of Wheatstone bridge circuits. Leads from the strain gages 314 are connected by wires 318 to a circuit monitoring device 320 which can measure the resistance and voltage across the gages 314.

When the handle portions 306, 308 of the tensioner 300 are compressed, i.e., moved toward each other, the separator portions 310, 312, by means of the pivot pin 316, move away from each other. If the separator portions 310, 312, when moved away each other, contact a generally immobile surface, continual compression of the handle portions 306, 308 will cause the separator portions 310, 312 to bend slightly in the vicinity of the strain gages 314. As the separator portions 310, 312 bend, the strain gages 314 are stretched or compressed, as appropriate, thereby changing the resistance of the resistors. As the resistance changes, the voltage across the strain gages 314 correspondingly changes, where the current in the circuit is constant. By monitoring the voltage, a surgeon can determine when a predetermined load has been reached, the voltage being representative of the predetermined load.

A method of creating a cavity in a vertebral body will now be described with respect to FIGS. 8-16. FIG. 8 shows the anterior aspects of two vertebral bodies 24 separated by an intervertebral disc 200. A cutting guide 20 is positioned on a side surface of the upper vertebral body 24 such that the walls 26, 30 having the concave edges are substantially parallel to the vertebral body endplates 208. The concave and convex portions 40, 42 of the cutting guide 20 are shaped so as to fit against the curved surface of the vertebral body 24. As the surface geometry of vertebral bodies varies somewhat between patients, typically either a three-point or four-point contact is achieved between the cutting guide 20 and the vertebral body 24.

As the cutting guide 20 is held against the vertebral body 24, a drill bit is journalled through one of the holes 44 in the cutting guide 20, and a hole is drilled into the vertebral body 24. A fastener 48 (e.g., drill bit, screw, nail, or pin) is then journalled through the hole 44 in the cutting guide and is received by the hole drilled into the vertebral body 24. If the fastener 48 is, for example, a screw, the screw would be turned into the hole in the vertebral body 24 by conventional means, thereby securing the cutting guide. 20 to the vertebral body 24. If the fastener 48 is a pin or a nail, it can be driven into the vertebral body 24 by tapping with a hammer or similar device. This process is then repeated for other holes 44 in the cutting guide 20 until the cutting guide is secured to the vertebral body 24. As a result, a plurality of fasteners 48 hold the cutting guide 20 onto the vertebral body 24. Although the figures disclose the use of four fasteners 48, any suitable number of fasteners can be used.

By journalling the fasteners 48 through the holes 44, the cutting guide 20 can slide off the fasteners 48 while the fasteners remain secured to the cortical bone 22, provided no part of the fasteners 48 has a diameter larger than the diameter of the holes 44. This ability to slide the cutting guide 20 facilitates removal of the cutting guide 20 (for purposes of removing a rectangular section 204 of cortical bone 22, as later described), while preserving the ability to reposition quickly the cutting guide 20 on the vertebral body 24 (for purposes of reaming the vertebral body 24, as later described). In addition, to avoid sliding the cutting guide 20 completely off of the fasteners 48, it is possible to use fasteners 48 having a length much greater than the cumulative depth of the cutting guide 20 and the holes drilled into the cortical bone. Using fasteners 48 of this nature will allow the surgeon to slide the cutting guide 20 away from the vertebral body 24 to a sufficient distance at which the cortical bone 22 of the vertebral body 24 can be accessed. In this regard, the surgeon can remove a generally rectangular section 204 of cortical bone 22 and then quickly and easily-reposition the cutting guide 20 on the vertebral body 24, as is necessary before the vertebral body's 24 interior cancellous bone may be removed by reamer 90, as later described.

Turning now to FIG. 9A, there is shown a vertebral body 24 having a cutting guide 20 affixed thereto. Positioned in the cutting guide 20 is a chisel guide 50 and a blade 82 of a chisel 62. The width W1 of the first block member 54 is less than or equal to the inner distance between two sidewalls 28, 30 of the cutting guide 20. The shoulders 56 and the ridge 76 on the second block 52 of the chisel guide 50 rest against the flat edge 36 of the cutting guide 20. In addition, the blade 82 of a chisel 62 is channeled through the passage 80 created between the cutting guide 20 and the chisel guide 50.

Once the blade 82 is positioned against the cortical bone 22 of the vertebral body 24, the free end of the chisel 60 can be tapped to drive the blade 82 into the cortical bone 22. In this manner, the chisel blade 82 punctures through the cortical bone 22 and cuts into the cancellous bone in the interior of the vertebral body 24, thereby forming a first cut. In a preferred embodiment, when the blade 82 of the chisel 62 is driven into the vertebral body 24 to a maximum allowable depth, the surface 63 on the chisel 62 abuts the second ridge 78 on the first block 54, thereby preventing the blade 82 from being driven further into the vertebral body 24. In this fashion, the surface 63 can act as a safety stop.

Due to the controlled manner of supporting the chisel 62 (i.e., by using the chisel guide 50), the surgeon can ensure a nearly straight cut through the bone 22 of the vertebral body 24. The nearly straight cut occurs along one side of an inside perimeter of the cavity 34 of the cutting guide 20. In addition, preferably fluoroscopy or radiographs are used to ensure that the transverse cuts made into and through the bone (to the depth limited by the surface 63 on the chisel 62 abutting the second ridge 78 on the first block 54) are generally parallel to the endplates 208 of the vertebral body 24.

Once the first transverse cut is made, the surgeon removes the chisel guide 50 from the cutting guide 20, rotates it 180 degrees toward an opposite wall 30, slides it back into the cutting guide 20, and creates a second cut into the cortical bone 22 of the vertebral body 24. This rotation will allow the surgeon to ensure that the cut made by the blade 82 of the chisel 62 is approximately parallel to the first cut.

After the first and second cuts are complete, the surgeon removes the chisel guide 50 and, if the cutting guide 20 is rectangular, inserts a second chisel guide. The width of the first block member of this second chisel guide is less than or equal to the inner distance between the upper and lower walls 26, 30 of the cutting guide 20. The second chisel guide is inserted into the cutting guide 20 at an orientation 90 degrees from the chisel-guide orientation shown in FIG. 3A, to create a passage for the chisel blade that is substantially perpendicular to the first and second cuts. In this position, a third cut can be made along wall 28. Next, the second chisel guide is rotated 180 degrees, in order that a fourth cut can be made along wall 32. The four completed cuts form a substantially rectangular cut 202 into the cortical bone 22 along an inner perimeter of the cutting guide 20.

Alternatively, the surgeon can chisel along the inner perimeter of the cutting guide 20 without using a chisel guide 50. Moreover, if a square cutting guide is employed, then only a single chisel guide would be necessary; after a first cut is made, that is, the chisel guide could be rotated 90, 180, and 270 degrees from its first orientation in the square cutting guide to make second, third, and fourth cuts, respectively, into the vertebral body 24.

FIG. 9B shows an alternative manner by which cuts can be made in the cortical bone 22 of the vertebral body 24. Rather than using a chisel 62 (with or without a chisel guide 50), the surgeon can use a sagittal saw 46 to make the cut into the cortical bone 22. The surgeon can also use the sagittal saw 46 to make preliminary shallow cuts in the cortical bone 22 and, afterward, use the chisel guide 50 and/or chisel 62 to make final cuts.

Figure 10:
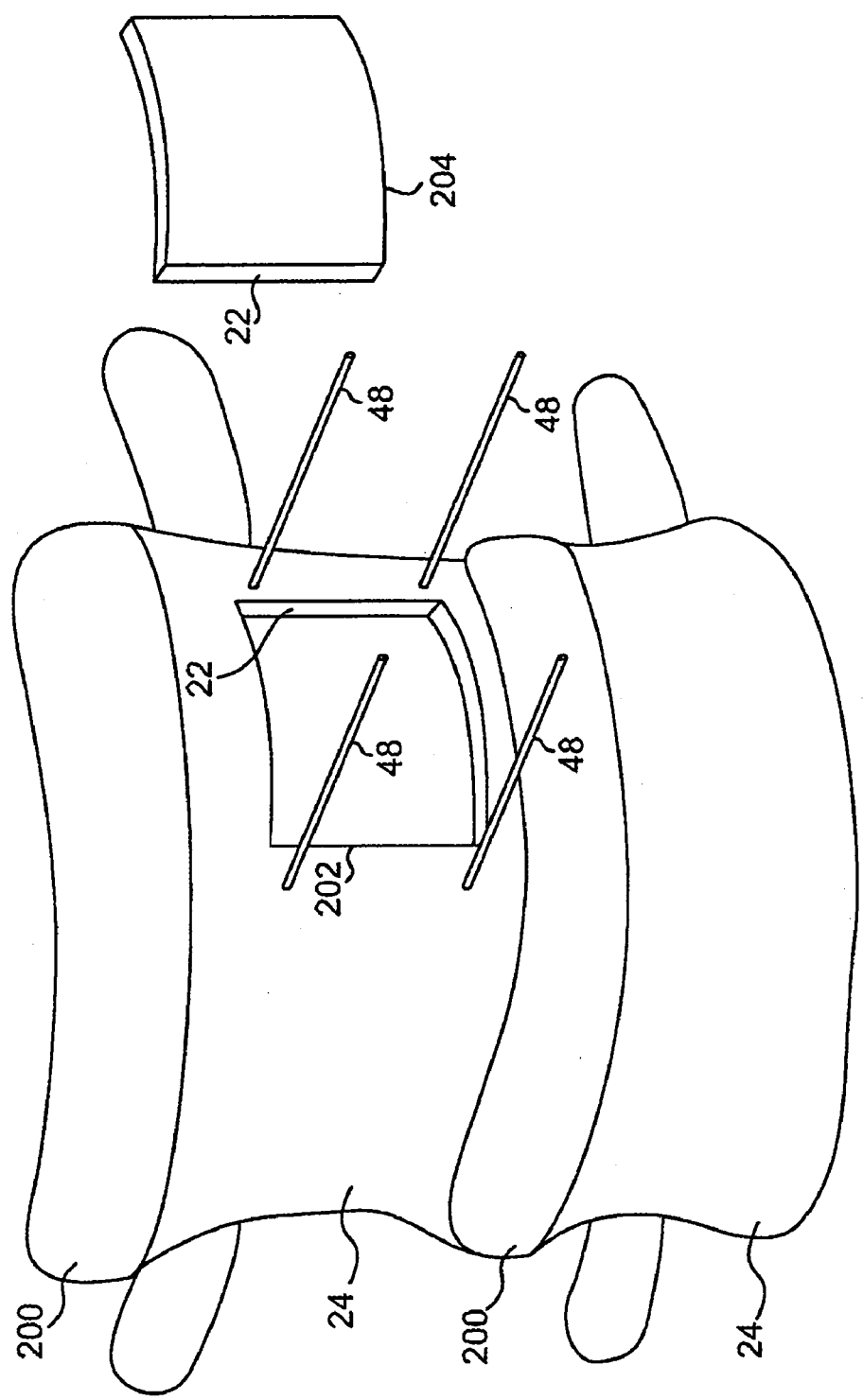
FIG. 10 is a schematic view of a vertebral body with a section of the cortical bone removed from the vertebral body.

As shown in FIG. 10, after cut 202 is made in the cortical bone 22, the cutting guide 20 is either removed or withdrawn along the fasteners 48 to a distance sufficient to allow access to the cortical bone 22 and the rectangular cut 202. In either case, some or all of the fasteners 48 can remain in the cortical bone 22 of the vertebral body. Once the cutting guide 20 is removed or withdrawn, section 204 of cortical bone 22 (defined by cut 202) is removed using an osteotome, thereby exposing the cancellous bone in the interior of the vertebral body 24. After the section 204 is removed, the cutting guide 20 is re-affixed to the vertebral body 24 by journalling the fasteners 48 projecting from the vertebral body 24 through the holes 44 in the cutting guide 20, as shown in FIG. 11.

Once the cutting guide 20 is re-affixed to the vertebral body 24, the surgeon can use a reamer 90 to drill a cavity 206 in the vertebral body 24 as shown in FIG. 11. The bone which is removed to form the cavity 206 is cut into bone shavings 118 by cutting implement 114 on the second end 116 of the reamer 90. The shavings 118 pass through the slots 120 in the end 116 of the reamer 90 and into the cavity 112 in the reamer 90. When the vertebral body cavity 206 is both wide enough and deep enough to accept a first fixation member 222 of a prosthetic device 220 which will rest in a cavity 206 of FIG. 12A, such as shown in FIG. 13, the surgeon stops reaming and removes the shavings 118 from the cavity 112 in the reamer 90. The shavings 118 can be used after implantation of a prosthetic device 220 to promote bone ingrowth into the prosthetic device 220, as later described. The first fixation member 222 then can be temporarily placed in the cavity and centered using fluoroscopy. If the first fixation member 222 cannot be properly centered (i.e., if the cavity 206 is slightly too mall), the surgeon can use a mechanical burr or curette to remove sufficient bone to allow the first fixation member 222 to fit within the cavity 206. The fixation member 222 then is removed from the cavity 206.

Figure 12A:
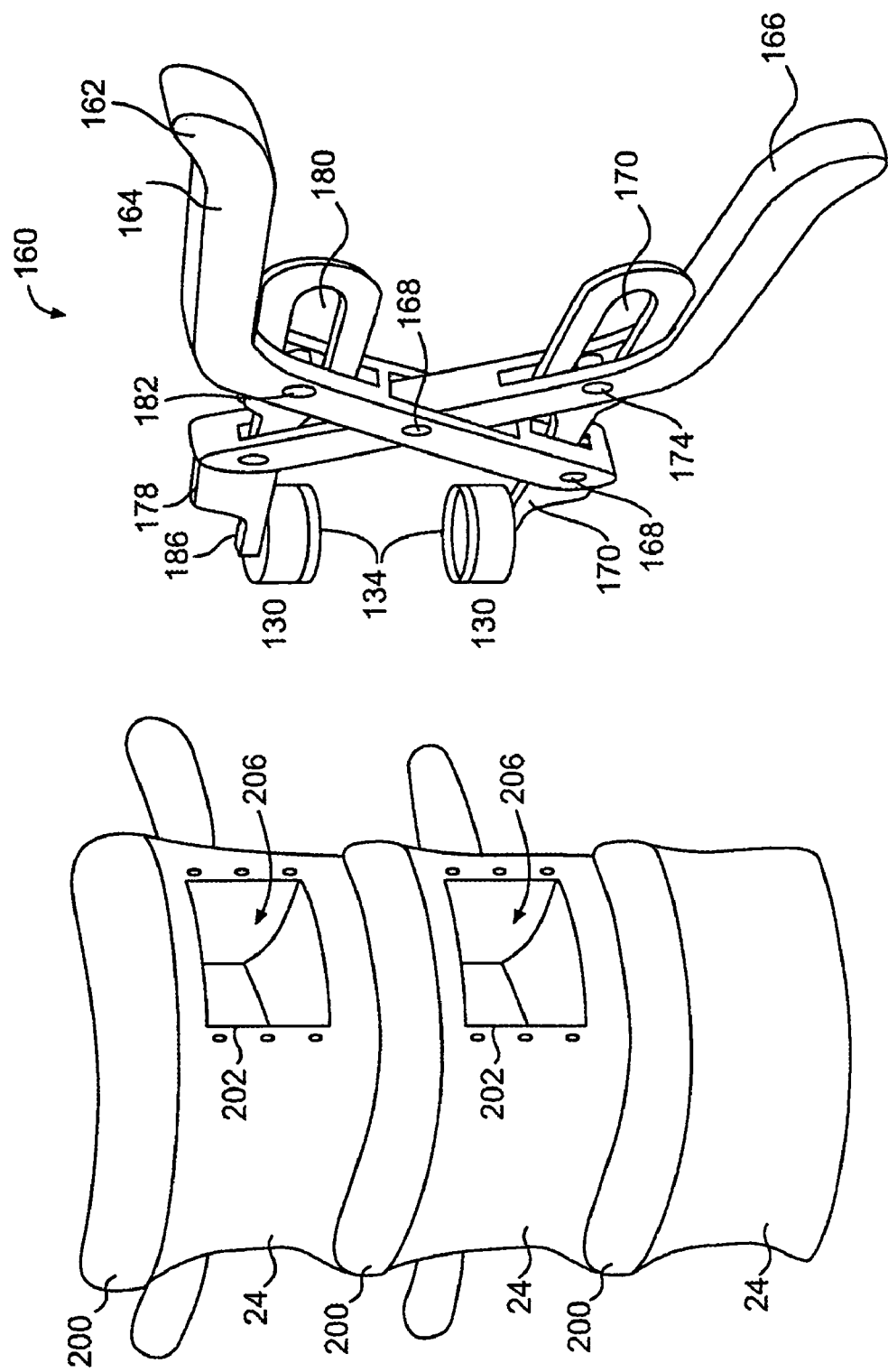
FIG. 12A is a schematic view of two adjacent vertebral bodies having cavities therein and a compressor having two endplate and nucleus cutters thereon.

After the cavity 206 is formed in the upper vertebral body 24, the surgeon goes through the same process with respect to the lower vertebral body 24 to form a cavity 206 therein, as shown in FIG. 12A. Once the two cavities 206 are created, the fasteners 48 can be removed from the cortical bone 22 of the vertebral bodies 24.

Figure 12B:
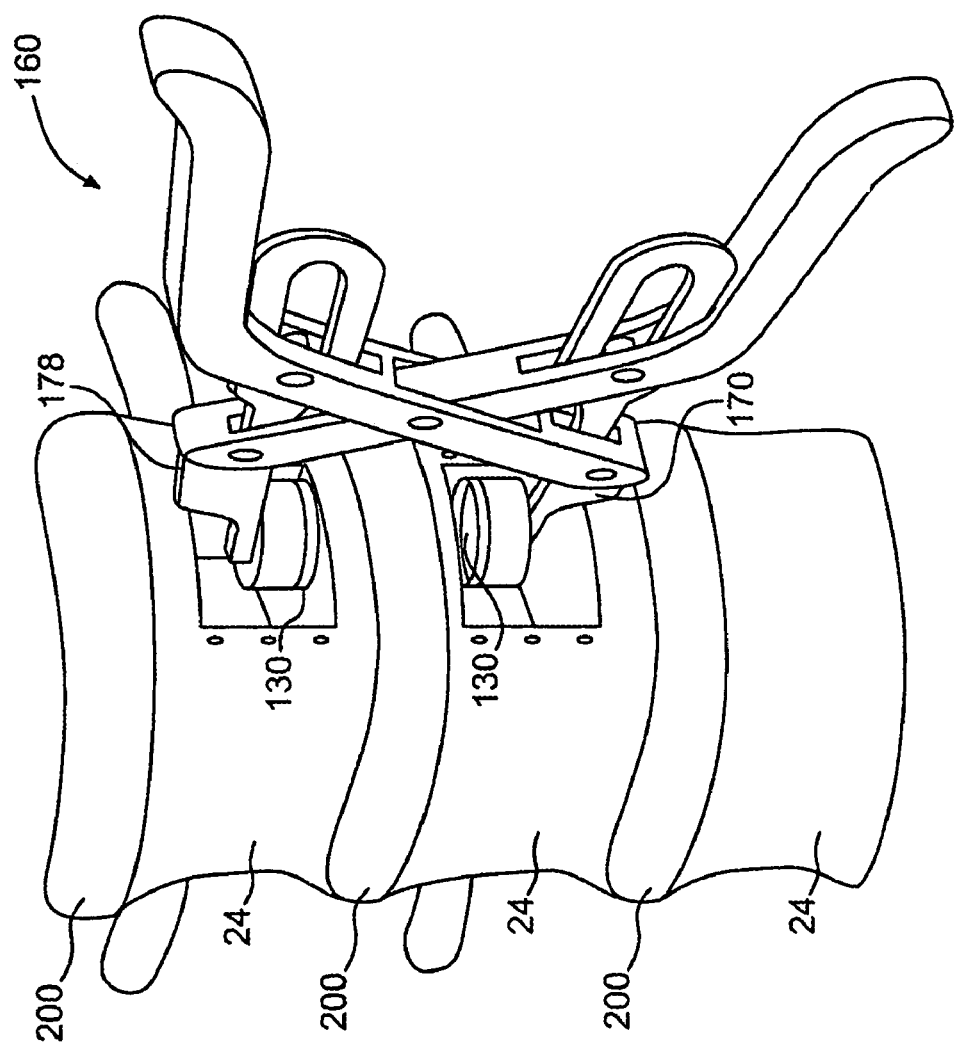
FIG. 12B is a schematic view of the compressor shown in FIG. 12A with the endplate and nucleus cutters inserted into the cavities of the adjacent vertebral bodies.

After the fasteners 48 are removed, a compressor 160, having cutting implements on each of its first and second arms 170, 178, is adjusted so that the cutting implements can simultaneously pass into the cavities 206 in the vertebral bodies 24. The cutting implements preferably are endplate and nucleus cutters 130. Prior to compression of the compressor 160, fluoroscopy can be used to ensure that the cutting implements are centered in the cavities 206 in the vertebral bodies 24.

Where endplate and nucleus cutters 130 are used as the cutting implements, upon compression of the handle 162, as shown in FIG. 12B, the two arms 170, 178 and the endplate and nucleus cutters 130 are brought towards each other. By compressing the handle 162, the generally circular cutting edges 134 of the endplate and nucleus cutters 130 move in an axial direction and cut through the endplates 208 (shown cut-through in FIG. 13) of the respective vertebral bodies 24 and then through the nucleus pulposus of the intervertebral disc 200 separating the vertebral bodies 24; the annulus fibrosis of the disc 200 remains intact. When the endplate and nucleus cutters 130 contact each other in a central portion of the disc 200, compression is stopped.

To facilitate cutting, the endplate and nucleus cutters 130 can be manually rotated during compression; that is, the compressor 160 can be twisted side-to-side during compression. Or, if the endplate and nucleus cutters 130 are mounted for mechanical rotation to the compressor arms 170, 178, the cutters 130 can be mechanically rotated during compression to facilitate cutting.

After the compressor 160, and its dual endplate and nucleus cutters 130, are removed from the vertebral bodies 24, the portions of the endplates 208 and the intervertebral disc 200, through which the generally circular cutting edges 134 of the endplate and nucleus cutters 130 were forced, are removed, thereby creating a generally cylindrical channel 212 from the lower vertebral body 24 through the intervertebral disc 200 and to the upper vertebral body 24. The channel 212, which is formed, in part, by the cavities 206 in the vertebral bodies 24, will hold the entire prosthetic device 220 as shown in FIG. 13.

A suitable prosthetic device for implantation in channel 212 is described in U.S. Pat. No. 5,827,328, incorporated herein by reference in its entirety. It is preferable that all parts of the prosthetic device 220, 230 be formed or machined from a biocompatible material, such as cobalt-chrome alloy. Initially, a compressible member 224 of an appropriate size and with appropriate angulation is selected based on the size and location of the disc 200 to be replaced and on the size of the patient. More specifically, choosing the proper compressible member 224 will depend both on the size of the annulus fibrosis in the particular disc 200 (which had its nucleus pulposus removed) and on the approximate lordosis of the motion segment level of the disc 200 that is being replaced. Once the compressible member 224, which may include a series of springs, is selected, it is inserted into the cavity 206 in one of the vertebral bodies 24. The compressible member 224 then is pushed into the hole in the intervertebral disc 200 that originally contained the nucleus pulposus. The compressible member 224 then is oriented so as to maintain lordosis (i.e., the thicker portions of the component 224 are placed anteriorly, as shown in FIG. 13).

After the compressible member 224 is in place, a first fixation member 222 is positioned in one of the cavities 206 in the vertebral bodies 24. The fixation member 222 is then connected to the compressible member 224, and the lordotic alignment is rechecked. Next, a second fixation member 222 is positioned in the cavity 206 in the other vertebral body 24 and is connected to the other side of the compressible member 224, thereby completing implantation of the prosthetic device 220.

Each of the fixation members 222 has an upper plate 260 and a lower plate 262. A plurality of vertically adjustable struts 264 are positioned between the upper and lower plates 260, 262. When the struts 264 are unlocked, their height can be easily changed. When the struts 264 are locked, their height remains constant.

Once the fixation members 222 are properly positioned in the vertebral bodies 24, the tension or load experienced by the compressible member 224 of the prosthetic device 220 needs to be adjusted to optimize the normal loading and compression (i.e., the functionality) of the particular disc 200 being replaced. To do so, the surgeon inserts the separator portions 310, 312 of a tensioner 300 into the upper one of the fixation members 222. Upon compression of the tensioner's handle portions 306, 308, the separator portions 310, 312 move away from each other into contact with the upper and lower plates 260, 262, respectively, forcing the plates 260, 262 toward the endplates 208 of the vertebral body 24. In this manner, the tensioner 300 elongates the fixation member 222 until a proper elongation distance between the plates 260, 262 is achieved. The separator portions 310, 312 preferably are positioned so that their tips contact the center of the plates 260, 262. As the plates 260, 262 move away from each other, the unlocked struts 264 will increase in length. When the upper plate 260 contacts the upper endplate 208 of the upper vertebral body, and the lower plate 262 contacts and encounters resistance from the compressible member 224, continual compression of the handle portions 306, 308 will cause a slight bending in the tensioner's separator portions 310, 312.

As previously described, the slight bending of the separator portions 310, 312 will deform the strain gages 314, thereby changing their resistance which, in turn, changes the voltage potential across the gages 314. By monitoring the change in voltage caused when the separator portions 310, 312 are opened (closed), and by amplifying and calibrating the voltage to known loads, a surgeon can determine whether the fixation member 222 has been suitably lengthened to properly tension, i.e., properly load, the compressible member 224. More specifically, the surgeon can calculate what load should be applied to a fixation member 222 to cause a desired corresponding reactive force or load from the compressible member 224; the more the surgeon expands the fixation member 222, the greater the reactive force from the compressible member 224. The voltage measured by the tensioner 300 is representative of the load applied to the fixation member 222. Thus, the surgeon uses the tensioner 300 to monitor the load applied to the fixation member 222. When the applied load equals a predetermined desired load, the surgeon knows that the fixation member 222 has been lengthened or elongated the appropriate amount to place the compressible member 224 under the proper degree of tension.

When the fixation member 222 reaches the proper length, the vertically adjustable struts 264 are locked, thereby maintaining proper tension or load in the compressible member 224. After the first fixation member 222 is properly lengthened, the same procedure may be used to properly lengthen the other fixation member 222 in the other vertebral body 24.

The struts 264 can be locked to maintain the proper length of the fixation member 222, i.e., the proper elongation distance between the upper and lower plates 260, 262, in a variety of ways. For example, the struts can be configured for adjustment like a crutch, that is, by having a hole through an outer casing and a plurality of holes through an adjustable inner member. When the inner member is adjusted to the proper height, a fastener can be inserted through the hole in one side of the casing, through the corresponding hole in the inner member, and then through the hole in the other side of the casing. The fastener immobilizes the inner member with respect to the casing and maintains the proper elongation distance between the upper and lower plates 260, 262.

Clamps also can be used to maintain the proper elongation distance between the plates 260, 262. The clamps are C-shaped in cross section and have a length equal to the elongation distance. The C-shaped cross section of the clamps leaves a slit or opening along their length. The clamps also are resiliently flexible. When the slit of a clamp is pressed against a strut, the slit widens so that the clamp can be slid around the strut. Once around the strut, the clamp returns to its initial shape. The clamps thus can be positioned on the struts 264 to substantially surround the struts 264 and maintain the proper elongation distance between the plates 260, 262.

A tripod also can be used to maintain the proper distance between the plates 260, 262. In this preferred method, the surgeon selects a tripod of an appropriate height, that is, of a height equal to the desired elongation distance, and slides it into the fixation member 222. The surgeon then positions the legs of the tripod on the lower plate 262, preferably against three struts 264, and positions the top of the tripod against the upper plate 260.

Figure 15:
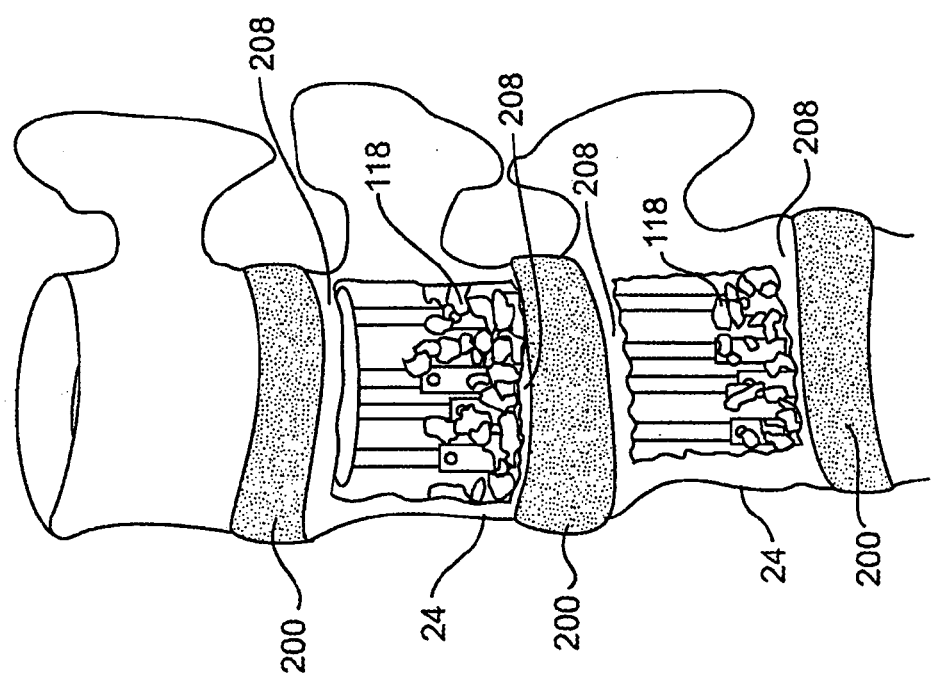
FIG. 15 is a schematic, cut-away left side view of the adjacent vertebral bodies having an intervertebral prosthetic device implanted therein, wherein the vertebral bodies are provided with bone shavings to induce bone grafting.

After the length of the fixation members 222 is fixed (i.e. by locking the struts 264 in each of the fixation members 222 when the proper amount of tension is experienced by the compressible member 224), the surgeon can use radiographs or fluoroscopy to confirm that the prosthetic device 220 is properly positioned and aligned. Once confirmed, the bone shavings 118 (bone graft) stored in the cavity 112 of the reamer 90 are placed into the cavities 206 in the vertebral bodies 24, as shown in FIG. 15. In time, the bone-shavings 118 will induce new bone to grow in the vertebral bodies 24 during the healing process. It is also possible to place bone cement, bone substitute, or bone morphogenic protein, rather than bone shavings 118, into the cavities 206. In addition, it is possible to use both bone cement combined with bone shavings 118.

Figure 16:
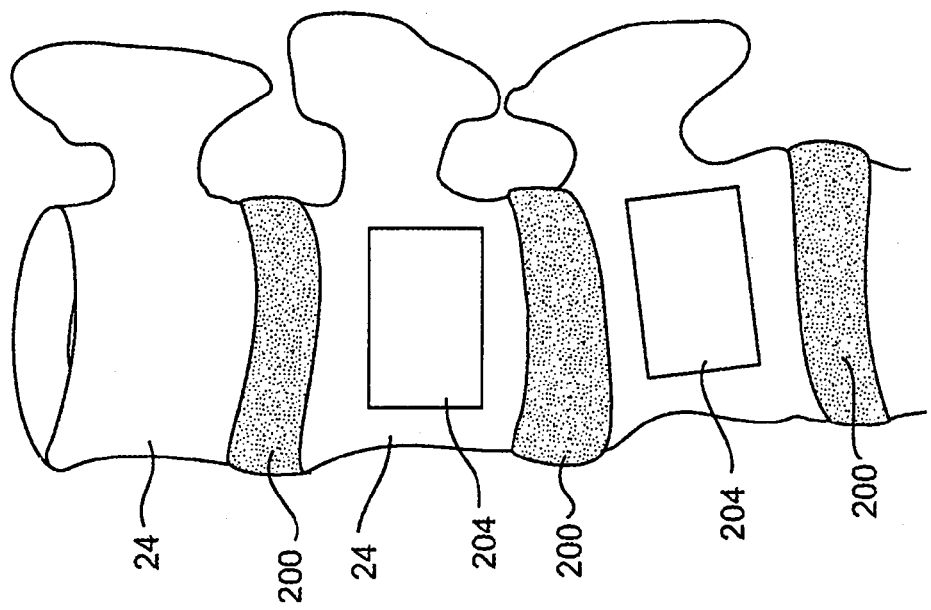
FIG. 16 is a schematic left side view of the adjacent vertebral bodies with the cortical bone repositioned to cover the cavities in the vertebral bodies.

As shown in FIG. 16, after the bone shavings 1118 and/or the bone cement are placed into the cavities 206 in the vertebral bodies 24, the pieces 204 of cortical bone 22 are replaced in the cuts 202 in the vertebral bodies 24 from which they came. The pieces 204 can be fixed to the vertebral bodies 24 using traditional methods, such as by a bone screw, plate, or bone cement, thereby enclosing the cavities 206 containing the bone shavings 118 and the prosthetic device 220.

Figure 17A:
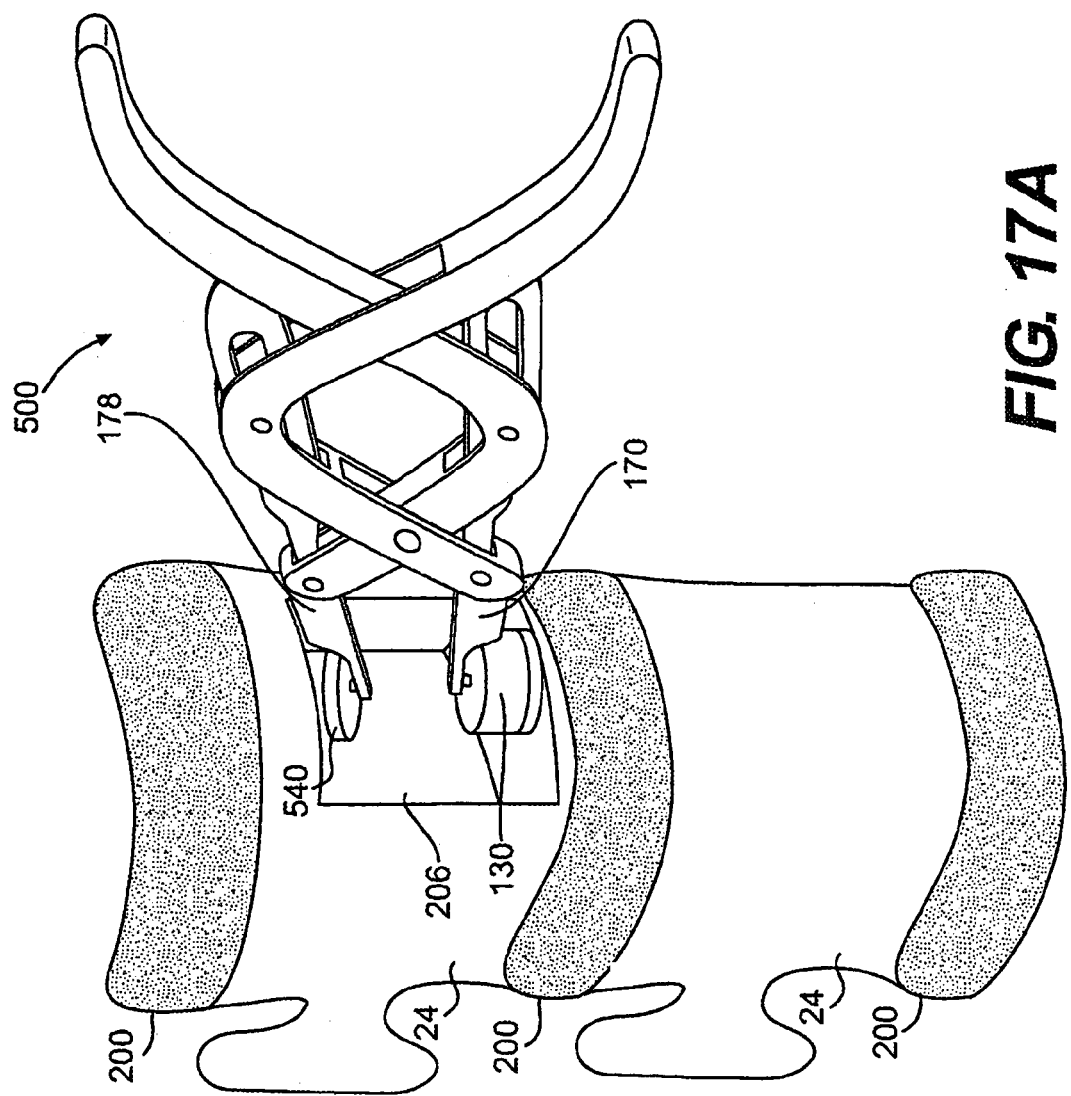
FIG. 17A is a schematic view of a vertebral body having a cavity therein and an alternative embodiment of the distractor having one endplate and nucleus cutter thereon.
Figure 17B:
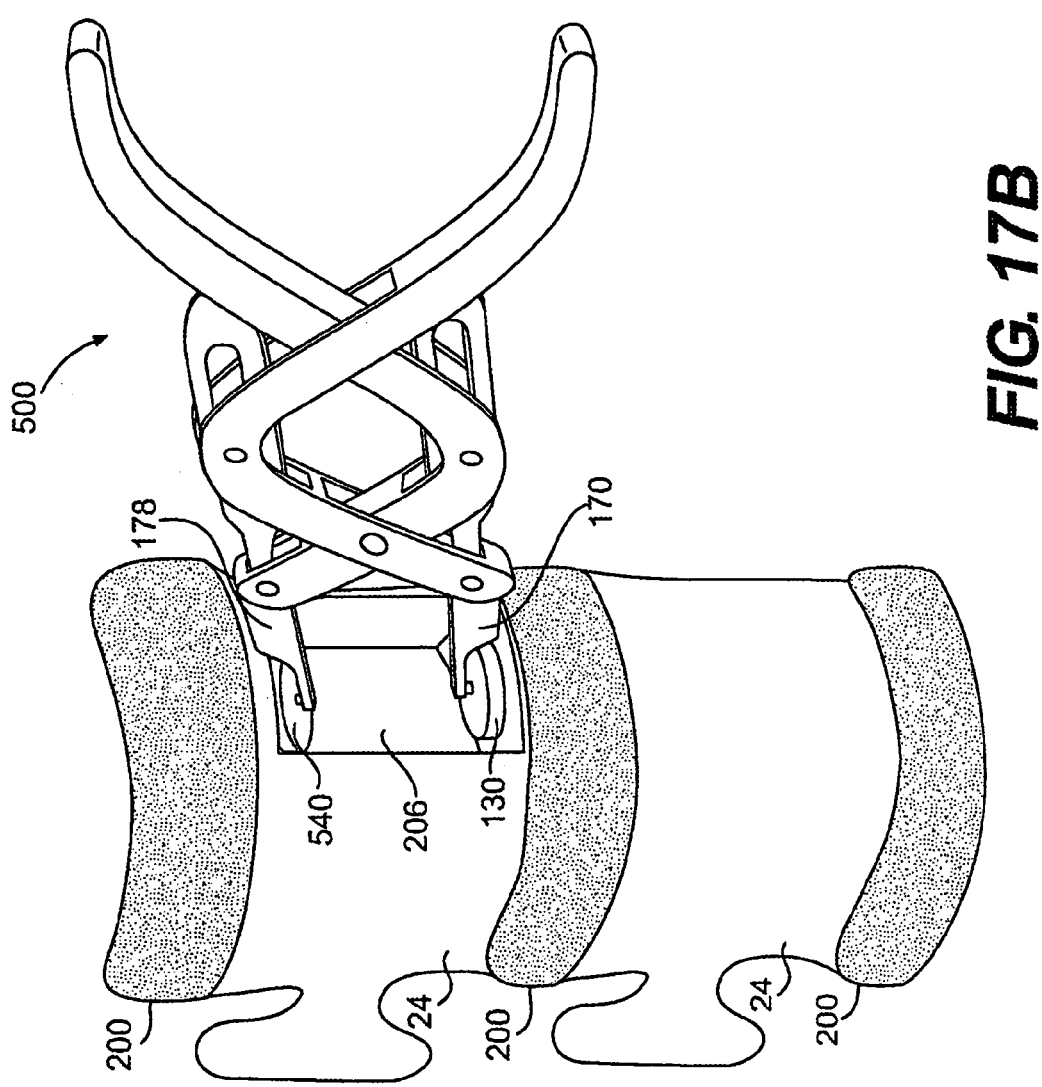
FIG. 17B is a schematic view of the distractor shown in FIG. 17A with the endplate and nucleus cutter inserted into the cavity of the vertebral body and forced downward into the nucleus pulposus of the intervertebral disc.

The aforementioned describes one method by which to create a cavity in an intervertebral disc. It is also possible, as shown in FIGS. 17A and 17B, to use a distractor 500 of the type shown in FIG. 6B to surgically implant a prosthetic device 230 through only one vertebral body 24. Specifically, after a cavity 206 is created in an upper (or lower) vertebral body 24 by a reamer 90 in the manner previously discussed, the scissor-like members 502, 504 of a distractor 500 are separated, thereby bringing the arms 510, 514 together. The arms 510, 514, having one outward facing cutting implement thereon, preferably an endplate and nucleus cutter 130, can then be inserted into the cavity 206.

When scissor-like members 502, 504 are compressed, the arms 514, 510 are separated, and the arm 514 having the endplate and nucleus cutter 130 thereon is pushed against the endplate 208 that is to be partially removed (to thereby provide access to the disc 200 below or above). As the handle 506 is compressed and, if necessary, twisted, the endplate and nucleus cutter 130 can be pushed downward (or upward) to cut through the endplate 208 of the vertebral body 24 and into the nucleus pulposus of the intervertebral disk 200 below (or above) the vertebral body 24. During this cutting process, the plate 540 on the opposite arm 510 acts as a brace by pushing against the endplate 208 above (or below) the endplate 208 through which the endplate and nucleus cutter 130 is forced. When the distractor 500 is twisted side to side, the plate 540 will remain fixed with respect to the endplate 208 against which it is positioned; this will prevent any inadvertent shaving of bone from the endplate 208 against which the plate 540 is positioned. In this manner, the endplate and nucleus cutter 130 makes a generally circular cut through the endplate 208 and into the intervertebral disc 200 below (or above) the endplate 208.

Once the cut has been made, the distractor 500 and endplate and nucleus cutter 130 attached thereto is removed from the cavity 206. The portion of the endplate 208 located within the generally circular cut may then be removed. In addition, the nucleus pulposus of the disk 200 can be removed using a commercially available soft tissue ablator, thereby forming a well 232, the location of which is shown in FIG. 18. The sides of the well 232 are formed by the remaining disk annulus, and the bottom of the well 232 is formed by non-removed disc 200 or by the endplate 208 of the vertebral body 24 below (or above) the intervertebral disc 200.

With respect to FIGS. 19A and 19B, after the well 232 is formed, the endplate 208 below (or above) the intervertebral disc 200 may then be prepared to accept an alternative disc prosthetic device 230. In this fashion, a rotating dome-shaped endplate reamer 400 can be used to abrade the endplate 208 on the side of the intervertebral disc 200 opposite the vertebral body 24 which accepted the distractor 500. The endplate reamer 400 creates a dome-shaped indentation 402 in the endplate 208 which corresponds to the shape of the side of the alternative disc prosthetic device 230 which will be positioned against it. In this manner, the endplate 208 is shaped to be congruent with the prosthetic device 230. In addition, the reamer 400 can be used to roughen the bone surface of endplate 208, which encourages bone ingrowth into the prosthetic device 230.

Upon removal of the nucleus pulposus of the disk 200, a prosthetic device 230 of the type shown in FIG. 18, i.e., a device having a compressible member 224 and one expandable fixation member 222, can be inserted into the well 232 and the cavity 206 in the vertebral body 24. Fluoroscopy is used to ensure that the device 230 is properly positioned, and a tensioner 300 is used, in the manner previously described, to determine whether the device is subject to the proper amount of loading. When the proper amount of loading is applied, the struts 264 in the device will be locked, in the manner previously described, to maintain the load. After the prosthetic device 230 is properly inserted and subject to the proper load, bone shavings 118 and/or bone cement can be poured into the cavity 206 in the vertebral body 24, as previously described. Finally, and similarly to the aforementioned manner of closing a cavity 206 in a vertebral body 24, the previously removed piece 204 of cortical bone 22 is repositioned and fused to the vertebral body 24.

For both of the previously described methods in which the nucleus pulposus of an intervertebral disk 200 is removed, it should be readily apparent to one of ordinary skill in the art these methods would be enhanced by a compressor 160 having or working in conjunction with motors to cause the endplate and nucleus cutters to rotate. Such rotation would make it easier for the cutting edge 134 of an endplate and nucleus cutter 130 to cut through both the endplate 208 of a vertebral body 24 and the nucleus pulposus of an intervertebral disc 200.

It also will be understood that the cutting guide 20, the chisel guide 50, the reamer 90, the compressor 160 and the distractor 500 and their associated endplate and nucleus cutters 130, the facing plate 540 of the distractor 500, the tensioner 300, the endplate reamer 400, and the chisel can be made of stainless steel or other suitable material.

Apparatuses and methods for performing spinal surgery have been described according to the present invention. Many modifications and variations may be made to the apparatuses and methods described and illustrated herein without departing from the spirit and scope of the invention. Accordingly, it should be understood that the apparatuses and methods described herein are illustrative only and are not limiting upon the scope of the invention.

What is claimed is:

1. A method of creating an intervertebral disc cavity, comprising:
    providing an apparatus including a first arm having a first cutting implement attached thereto, a second arm, and a handle,
    positioning the first arm in a first vertebral body cavity in a first vertebral body adjacent an intervertebral disc;
    compressing the handle so that the first and second arms move relative to each other;
    cutting into the nucleus pulposus of the intervertebral disc with the first cutting implement; and
    removing the nucleus pulposus of the intervertebral disc to create the intervertebral disk cavity.

2. The method according to claim 1, further comprising positioning the second arm in a second vertebral body cavity in a second vertebral body, wherein the second arm has a second cutting implement thereon.

3. The method according to claim 2, further comprising cutting into the nucleus pulposus of the intervertebral disc with the second cutting implement.

4. The method according to claim 2, further comprising:
    attaching a cutting guide to a surface of the first vertebral body;
    cutting through the surface and cortical bone of the first vertebral body;
    removing the cut cortical bone of the first vertebral body to expose bone in an interior of the first vertebral body;
    removing the bone in the interior of the first vertebral body to create the first vertebral body cavity;
    removing the cutting guide from the first vertebral body;
    attaching the cutting guide to a surface of the second vertebral body;
    cutting through the surface and cortical bone of the second vertebral body;
    removing the cut cortical bone of the second vertebral body to expose the bone in the interior of the second vertebral body; and
    removing the bone in the interior of the second vertebral body to create the second vertebral body cavity.

5. The method according to claim 1, further comprising:
    attaching a cutting guide to a surface of the first vertebral body;
    cutting through the surface and cortical bone of the first vertebral body;
    removing the cut cortical bone of the first vertebral body to expose bone in an interior of the first vertebral body;
    removing the bone in the interior of the first vertebral body to create the first vertebral body cavity; and
    removing the cutting guide from the first vertebral body.

6. The method according to claim 1, further comprising:

positioning the second arm in the first vertebral body cavity in the first vertebral body, wherein the second arm has a plate thereon.

7. A method of creating an intervertebral disc cavity, comprising:

providing an apparatus including a first arm having a cutting implement attached thereto, a second arm, and a handle, positioning the first and second arms in a cavity in a vertebral body;

compressing the handle so that the first and second arms move in a direction away from each other;

cutting into the nucleus pulposus of the intervertebral disc with the cutting implement; and removing the nucleus pulposus of the intervertebral disc to create the intervertebral disk cavity.

8. The method according to claim 7, further comprising:

attaching a cutting guide to a surface of the vertebral body;

cutting through the surface and cortical bone of the vertebral body;

removing the cut cortical bone of the vertebral body to expose bone in an interior of the vertebral body;

removing the bone in the interior of the vertebral body to create the vertebral body cavity; and removing the cutting guide from the vertebral body.

9. The method according to claim 7, further comprising:

providing a plate on the second arm; and positioning the plate against a first endplate of the vertebral body opposite a second endplate through which the cutting implement is pushed when the handle is compressed.

10. A method of creating an intervertebral disc cavity, comprising:

providing an apparatus including a first arm having a first cutting implement attached thereto, a second arm having a second cutting implement attached thereto, and a handle, positioning the first arm in a first vertebral body cavity in a first vertebral body adjacent an intervertebral disc;

positioning the second arm in a second vertebral body cavity in a second vertebral body adjacent the intervertebral disc;

compressing the handle so that the first and second arms move in a direction towards each other;

cutting into the nucleus pulposus of the intervertebral disc with the first cutting implement; and removing the nucleus pulposus of the intervertebral disc to create the intervertebral disk cavity.

* * * * *